United States Patent
Mylari et al.

(10) Patent No.: US 9,382,187 B2
(45) Date of Patent: Jul. 5, 2016

(54) TRI-SALT FORM OF METFORMIN

(71) Applicant: Thetis Pharmaceuticals LLC, Southport, CT (US)

(72) Inventors: Banavara L. Mylari, Lutz, FL (US); Frank C. Sciavolino, Waterford, CT (US)

(73) Assignee: Thetis Pharmaceuticals LLC, Southport, CT (US)

( * ) Notice: Subject to any disclaimer, the term of this patent is extended or adjusted under 35 U.S.C. 154(b) by 0 days.

(21) Appl. No.: 14/413,996

(22) PCT Filed: Jul. 10, 2013

(86) PCT No.: PCT/US2013/049984
§ 371 (c)(1),
(2) Date: Jan. 9, 2015

(87) PCT Pub. No.: WO2014/011814
PCT Pub. Date: Jan. 16, 2014

(65) Prior Publication Data
US 2015/0197475 A1    Jul. 16, 2015

Related U.S. Application Data

(63) Continuation-in-part of application No. 13/841,970, filed on Mar. 15, 2013.

(60) Provisional application No. 61/670,368, filed on Jul. 11, 2012, provisional application No. 61/670,376, filed on Jul. 11, 2012, provisional application No. 61/669,763, filed on Jul. 10, 2012.

(51) Int. Cl.
| | |
|---|---|
| *A61K 31/36* | (2006.01) |
| *C07C 57/03* | (2006.01) |
| *A61K 31/155* | (2006.01) |
| *A61K 45/06* | (2006.01) |
| *C07C 51/347* | (2006.01) |
| *C07C 229/24* | (2006.01) |
| *A61K 38/28* | (2006.01) |
| *C07C 279/26* | (2006.01) |
| *C07C 51/41* | (2006.01) |

(52) U.S. Cl.
CPC ............... *C07C 57/03* (2013.01); *A61K 31/155* (2013.01); *A61K 38/28* (2013.01); *A61K 45/06* (2013.01); *C07C 51/347* (2013.01); *C07C 51/412* (2013.01); *C07C 229/24* (2013.01); *C07C 279/26* (2013.01)

(58) Field of Classification Search
None
See application file for complete search history.

(56) References Cited

U.S. PATENT DOCUMENTS

| | | | |
|---|---|---|---|
| 5,795,909 | A | 8/1998 | Shashoua et al. |
| 6,372,790 | B1 * | 4/2002 | Bonhomme ......... A61K 31/195 514/555 |
| 6,491,950 | B1 | 12/2002 | Gutierrez-Rocca et al. |
| 6,517,870 | B1 | 2/2003 | Nishii et al. |
| 6,602,902 | B2 | 8/2003 | Shashoua et al. |
| 6,667,064 | B2 | 12/2003 | Surette |
| 6,720,001 | B2 | 4/2004 | Chen et al. |
| 6,881,854 | B2 | 4/2005 | Ptock et al. |
| 6,893,627 | B2 | 5/2005 | Ribnicky et al. |
| 7,105,572 | B2 | 9/2006 | Sato |
| 7,195,914 | B2 | 3/2007 | Surette |
| 7,199,151 | B2 | 4/2007 | Shashoua et al. |
| 7,214,387 | B2 | 5/2007 | Sanghvi et al. |
| 7,223,770 | B2 | 5/2007 | Zhang et al. |
| 7,304,089 | B2 | 12/2007 | Kramer et al. |
| 7,429,395 | B2 | 9/2008 | Campbell-Tofte |
| 7,553,870 | B2 | 6/2009 | Shibuya |
| 7,579,025 | B2 | 8/2009 | Campbell-Tofte |
| 7,619,002 | B2 | 11/2009 | Shibuya |
| 7,666,898 | B2 | 2/2010 | Chang et al. |
| 7,670,612 | B2 | 3/2010 | Miller |
| 7,973,073 | B2 | 7/2011 | Mylari et al. |
| 8,058,312 | B2 | 11/2011 | Kim et al. |
| 8,076,377 | B2 | 12/2011 | Kim et al. |
| 8,765,811 | B2 | 7/2014 | Mylari et al. |
| 8,933,124 | B2 | 1/2015 | Mylari et al. |
| 2003/0220301 | A1 | 11/2003 | Lal et al. |
| 2005/0158374 | A1 | 7/2005 | Wong et al. |

(Continued)

FOREIGN PATENT DOCUMENTS

| | | |
|---|---|---|
| WO | WO-02/12177 A1 | 2/2002 |
| WO | WO-03068209 A1 | 8/2003 |

(Continued)

OTHER PUBLICATIONS

Sugiyama et al. in Life Sciences 83 (2008) 19-28.*
Cold Spring Harbor Protocols 2006 (retrieved from the internet Nov. 13, 2013).*
"Amino Acid pKa Values" in www.cem.msu.edu/~cem 252/sp97/ch24/ch24aa.html (retrieved from the internet Nov. 14, 2013).*

(Continued)

*Primary Examiner* — Dennis Heyer
(74) *Attorney, Agent, or Firm* — Mintz Levin Cohn Ferris Glovsky and Popeo, P.C.; Muriel Liberto, Esq.

(57) ABSTRACT

Provided herein are tri-salt compounds comprising a compound having two acidic functional groups and one basic functional groups (e.g., aspartate or glutamate), metformin, and polyunsaturated fatty acids, such as eicosapentaenoate or docosahexaenoate. The salts can be used in the treatment of diabetes, diabetes with concomitant dyslipidemia (e.g., high triglycerides) and diabetes exacerbated cardiovascular complications, such as cardiac arrhythmia, cardiac ischemia, myocardial infarction, cardiomyopathy, and stroke. The compounds of this invention are also useful in treating obesity.

40 Claims, No Drawings

(56) References Cited

U.S. PATENT DOCUMENTS

| | | |
|---|---|---|
| 2005/0182029 A1 | 8/2005 | Lal |
| 2006/0159746 A1 | 7/2006 | Troup et al. |
| 2006/0229359 A1 | 10/2006 | Zhang et al. |
| 2006/0240095 A1 | 10/2006 | Junien et al. |
| 2007/0060532 A1 | 3/2007 | Junien et al. |
| 2007/0207196 A1 | 9/2007 | Zhang |
| 2008/0045559 A1 | 2/2008 | Zhang et al. |
| 2008/0200533 A1 | 8/2008 | Krishnan |
| 2008/0260819 A1 | 10/2008 | Fleming et al. |
| 2009/0047340 A1 | 2/2009 | Guilford |
| 2009/0054513 A1 | 2/2009 | Webster et al. |
| 2009/0156612 A1 | 6/2009 | Kuroita et al. |
| 2009/0227560 A1 | 9/2009 | Kuroita et al. |
| 2010/0035990 A1 | 2/2010 | Bryhn et al. |
| 2010/0105773 A1 | 4/2010 | Smith et al. |
| 2010/0121048 A1 | 5/2010 | Kuroita et al. |
| 2010/0137587 A1 | 6/2010 | Takanobu et al. |
| 2010/0324010 A1 | 12/2010 | Imaeda et al. |
| 2011/0046053 A1 | 2/2011 | Kidron |
| 2011/0052678 A1 | 3/2011 | Shantha et al. |
| 2011/0171142 A1 | 7/2011 | Lara |
| 2012/0178813 A1 | 7/2012 | Mylari et al. |
| 2013/0095140 A1 | 4/2013 | Baron et al. |
| 2014/0100273 A1 | 4/2014 | Bobotas et al. |
| 2014/0118419 A1 | 5/2014 | Wu et al. |
| 2014/0249221 A1 | 9/2014 | Mylari et al. |

FOREIGN PATENT DOCUMENTS

| | | |
|---|---|---|
| WO | WO-2005042539 A1 | 5/2005 |
| WO | WO-2005118612 A1 | 12/2005 |
| WO | WO-2009038396 A2 | 3/2009 |
| WO | WO-2010127099 A2 | 11/2010 |

OTHER PUBLICATIONS

"prandimet-drug" in www.rxlist.com/prandimet-drug.htm (retrieved from the internet Nov. 14, 2013).*

"eicosapentaenoic acid pKa" retrieved from STN Registry File Nov. 14, 2013.*

Junien et al. in US 2006/0240095 (published Oct. 26, 2006).*

"Amino Acid Structures." Web. Nov. 14, 2013. http://www.cem.msu.edu/~cem252/sp97/ch24/ch24aa/html.

"Cold Spring Harbor Protocols." 2006. Web. Nov. 13, 2013. http://cshprotocols.cship.org.

"Eicosapentaenoic Acid pKa." STN Registry File. Web. Nov. 14, 2013.

"Prandimet." RxList. Web. Nov. 14, 2013. http://www.rxlist.com/prandimet-drug.htm.

Charles et al. "Treatment with Metformin of Non-Diabetic Men with Hypertension, Hypertriglyceridaemia and Central Fat Distribution: The BIGPRO 1.2 Trial." *Diabetes Metab. Res. Rev.* 16(2000):2-7.

Goldberg et al. "Lifestyle and Metformin Treatment Favorably Influence Lipoprotein Subfraction Distribution in the Diabetes Prevention Program." *J. Clin. Endocrinol. Metab.* pub. ahead of print Aug. 26, 2013.

Sugiyama et al. "Eicosapentaenoic Acid Lowers Plasma and Liver Cholesterol Levels in the Presence of Peroxisome Profferators-Activate Receptor Alpha." *Life Sciences.* 83(2008):19-28.

Wulffelé et al. "The Effect of Metformin on Blood Pressure, Plasma Cholesterol and Triglycerides in Type 2 Diabetes Mellitus: A Systematic Review." *J. Intern. Med.* 256.1(2004):1-14.

International Search Report issued in PCT/US2013/049984 on Nov. 28, 2013.

* cited by examiner

TRI-SALT FORM OF METFORMIN

RELATED APPLICATIONS

This application is a 35 U.S.C. §371 national stage entry of PCT/US2013/049984, filed Jul. 10, 2013, which claims priority to U.S. Provisional Application No. 61/669,763, filed Jul. 10, 2012; U.S. Provisional Application No. 61/670,376, filed Jul. 11, 2012; U.S. Provisional Application No. 61/670,368, filed Jul. 11, 2012; and U.S. application Ser. No. 13/841,970, filed Mar. 15, 2013. The contents of all of these applications are incorporated herein by reference in their entireties.

BACKGROUND OF THE INVENTION

Diabetes mellitus has become pandemic and according to a forecast by the World Health Organization, there will be a sharp increase in the number of diabetic patients by the year 2030. This is an ominous forecast, because managing the long-term complications of diabetes, which include nephropathy, neuropathy, retinopathy, and cardiovascular complications, will have a serious impact on public health budgets. The hallmark of diabetes is chronically elevated blood glucose levels. It is also known that abnormally elevated glucose levels have an adverse impact on glutathione levels in key diabetic tissues. Furthermore, increased oxidative stress and increased production of reactive oxygen species are implicated under hyperglycemic conditions.

In spite of the early discovery of insulin and its subsequent widespread use in the treatment of diabetes, and the later discovery of and use of sulfonylureas, and thiazolidenediones, such as troglitazone, rosiglitazone or pioglitazone, and DPPIV inhibitors such as sitagliptin as oral hypoglycemic agents, the treatment of diabetes remains less than satisfactory.

The use of insulin requires multiple daily doses, usually by self-injection. Determination of the proper dosage of insulin requires frequent estimations of the sugar in urine or blood. Treatment of non-insulin dependent diabetes mellitus (Type II diabetes, NIDDM) usually consists of a combination of diet, exercise, oral hypoglycemic agents, e.g., thiazolidenediones, and, in more severe cases, insulin. However, the clinically available hypoglycemic agents can either have side effects limiting their use, or an agent may not be effective with a particular patient. In the case of insulin dependent diabetes mellitus (Type I), insulin administration usually constitutes the primary course of therapy.

Accordingly, there remains a need for an effective treatment of diabetes, type 2 diabetes (T2D), and pre-diabetes, as well as related conditions, such as neuropathy, nephropathy, retinopathy, cataracts and cardiovascular complications, including cardiac arrhythmia, myocardial infarction, stroke, and cardiomyopathy in diabetic patients.

SUMMARY OF THE INVENTION

Provided herein are tri-salt compounds comprising aspartate, glutamate, or homologues thereof, metformin, and polyunsaturated fatty acids, such as eicosapentaenoate or docosahexaenoate. The tri-salt compounds can be used in the treatment of diabetes, diabetes with concomitant dyslipidemia (e.g., high triglycerides) and diabetes exacerbated cardiovascular complications, such as cardiac arrhythmia, cardiac ischemia, myocardial infarction, cardiomyopathy, and stroke. The tri-salt compounds are also useful in treating obesity.

Provided herein are tri-salts of a compound with two acidic functional groups and one basic functional group, metformin, and a polyunsaturated fatty acid, which are represented by the following Formula I:

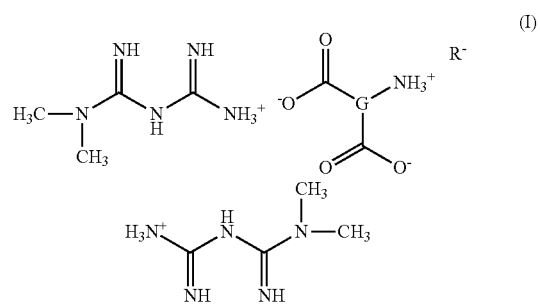

wherein G is an alkyl, cycloalkyl, heteroalkyl, heterocyclyl, aryl, or heteroaryl group; and $R^-$ is a polyunsaturated fatty acid. In an embodiment of Formula I, G is alkyl.

In a particular embodiment, compounds of Formula I are of the Formula II:

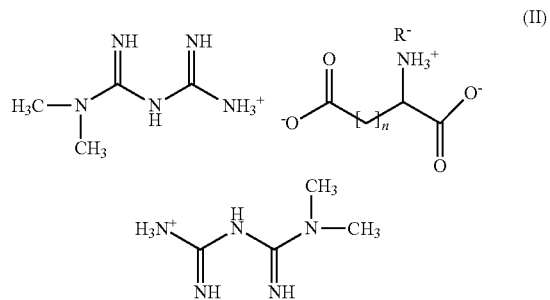

wherein $R^-$ is a polyunsaturated fatty acid, and n is 1-10, or a pharmaceutically acceptable solvate or hydrate thereof. In a particular embodiment of Formula II, n is 1 or 2. In another particular embodiment, n is 3, 4, or 5.

In an embodiment of Formulas I and II, $R^-$ is eicosapentaenoate or docosahexaenoate. In an embodiment of Formula II, $R^-$ is eicosapentaenoate or docosahexaenoate, and n is 1. In still another embodiment of Formula II, $R^-$ is eicosapentaenoate or docosahexaenoate, and n is 2.

Also provided herein is a pharmaceutical composition comprising a compound of Formula I, and a pharmaceutically acceptable carrier, vehicle or diluent.

Also provided herein is a kit comprising a unit dosage comprising a compound of the invention with instructions on how to use the kit and at least one container for holding the unit dosage form.

The compounds of Formula I can be used in the treatment of a number of diseases and indications. Accordingly, in one aspect, provided herein is a method for treating diabetes in a subject in need thereof, comprising administering to the subject a therapeutically effective amount of a compound of Formula I. In another aspect, provided herein is a method of lowering triglycerides in a subject in need thereof, comprising administering to the subject a therapeutically effective amount of a compound of Formula I. In still another aspect, provided herein is a method for treating cardiovascular diseases in a subject in need thereof, comprising administering to the subject a therapeutically effective amount a compound of Formula I. Examples of cardiovascular diseases to be treated are cardiac arrhythmia, cardiac ischemia, myocardial infarction, cardiomyopathy, or stroke.

In another aspect, provided herein is a method for treating obesity in a subject in need thereof, comprising administering to the subject a therapeutically effective amount of a compound of Formula I.

In one aspect, provided herein is a method of treating hyperlipidemia, comprising administering to a subject in need thereof an effective amount of a compound of Formula I. In another aspect, provided herein is a method of treating hypertriglyceridemia, comprising administering to a subject in need thereof an effective amount of a compound of Formula I. In another aspect, provided herein is a method of treating dyslipidemia, comprising administering to a subject in need thereof an effective amount of a compound of Formula I.

In another aspect, provided herein is a method of treating prediabetes, comprising administering to a subject in need thereof an effective amount of a compound of the invention. In still another aspect, provided herein is a method of treating atherosclerosis, comprising administering to a subject in need thereof an effective amount of a compound of the invention. In another aspect, provided herein is a combination therapy comprising a compound of the structural Formula I or II above, and an antihyperlipidemic agent, to treat a metabolic disorder selected from the group consisting of T2D, pre-diabetes, obesity, metabolic syndrome, hypertriglyceridemia and T2D complications such as neuropathy, nephropathy, retinopathy, cataracts and cardiovascular complications, including atrial fibrillation, cardiac arrhythmia, myocardial infarction, stroke, and cardiomyopathy in mammals, e.g., diabetic patients. An additional aspect provided herein is combination therapy comprising a compound of the structural Formula I or II and an antihyperlipidemic agent, to treat obesity, cardiovascular disease, and related indications in a subject in need thereof.

In yet another aspect, provided herein is a combination therapy comprising a compound of the structural Formula I or II above, and an antihyperglycemic agent, to treat a metabolic disorder selected from the group consisting of type 2 diabetes (T2D), pre-diabetes, obesity, metabolic syndrome, hypertriglyceridemia and T2D complications such as neuropathy, nephropathy, retinopathy, cataracts and cardiovascular complications, including cardiac arrhythmia, myocardial infarction, stroke, and cardiomyopathy in mammals, e.g., diabetic patients.

Accordingly, in one aspect, provided herein is a method for treating diabetes in a subject in need thereof, comprising administering to the subject a therapeutically effective amount of the combination therapy described above. In another aspect, provided herein is a method of lowering triglycerides in a subject in need thereof, comprising administering to a subject in need thereof an effective amount of the combination therapy of the invention. In still another aspect, provided herein is a method for treating cardiovascular diseases in a subject in need thereof, administering to a subject in need thereof an effective amount of the combination therapy of the invention. Examples of cardiovascular diseases to be treated are cardiac arrhythmia, cardiac ischemia, myocardial infarction, cardiomyopathy, or stroke.

In another aspect, provided herein is a method for treating obesity in a subject in need thereof, administering to a subject in need thereof an effective amount of the combination therapy of the invention.

In one aspect, provided herein is a method of treating hyperlipidemia, administering to a subject in need thereof an effective amount of the antihyperlipidemic combination therapy of the invention. In another aspect, provided herein is a method of treating hypertriglyceridemia, administering to a subject in need thereof an effective amount of the antihyperlipidemic combination therapy of the invention. In another aspect, provided herein is a method of treating dyslipidemia, administering to a subject in need thereof an effective amount of the antihyperlipidemic combination therapy of the invention.

In another aspect, provided herein is a method of treating prediabetes, administering to a subject in need thereof an effective amount of the combination therapy of the invention.

In still another aspect, provided herein is a method of treating atherosclerosis, administering to a subject in need thereof an effective amount of the combination therapy of the invention. In one embodiment of the above methods, the subject is human.

Also provided herein are methods of making the compounds of Formula II. In one aspect, provided herein is a method for the manufacture of a compound of Formula II, wherein $R^-$ is eicosapentaenoate and n is 1, comprising: a) preparing the free base of metformin from a metformin salt; and b) reacting two equivalents of the free base of metformin with one equivalent of aspartic acid one equivalent of eicosapentaenoic acid at a temperature between about 1° C. and about 60° C.

In another aspect, provided herein is a method for the manufacture of a compound of Formula II, wherein $R^-$ is eicosapentaenoate and n is 2, comprising: a) preparing the free base of metformin from a metformin salt; and b) reacting two equivalents of free base of metformin with one equivalent of glutamic acid one equivalent of eicosapentaenoic acid at a temperature between about 1° C. and about 60° C.

In another aspect, provided herein is a method for the manufacture of a compound of Formula II, wherein $R^-$ is docosahexaenoate and n is 1, comprising: a) preparing the free base of metformin from a metformin salt; and b) reacting two equivalents of the free base of metformin with one equivalent of aspartic acid one equivalent of eicosapentaenoic acid at a temperature between about 1° C. and about 60° C.

In yet another aspect, provided herein is a method for the manufacture of a compound of Formula II, wherein $R^-$ is docosahexaenoate and n is 2, comprising: a) preparing the free base of metformin from a metformin salt; and b) reacting two equivalents of free base of metformin with one equivalent of glutamic acid one equivalent of eicosapentaenoic acid at a temperature between about 1° C. and about 60° C.

DETAILED DESCRIPTION OF THE INVENTION

Metabolic syndrome is intricately intertwined with T2D, which has become pandemic. Clinical presentation of this syndrome is patient-dependent and the co-morbidities in patients with diabetes (chronic hyperglycemia) include high blood pressure, hyperlipidemia and cardiovascular complications, including stroke, myocardial ischemia and cardiomyopathy. The long-term consequences of these co-morbidities also include diabetic nephropathy, diabetic neuropathy, diabetic retinopathy and diabetic cataracts.

Metformin is a known compound approved by the U.S. Food & Drug Administration for the therapeutic treatment of diabetes. The compound and its preparation and use are disclosed, for example, in U.S. Pat. No. 3,174,901. Metformin is orally effective in the treatment of type 2 diabetes (T2D). Metformin (N,N-dimethylimidodicarbonimidic diamide) is a biguanide, anti-hyperglycemic agent currently marketed in the United States in the form of its hydrochloride salt 1,1- dimethylbiguanide hydrochloride. Metformin hydrochloride can be purchased commercially and it can also be prepared, for example, as disclosed in J. Chem. Soc., 1922, 121, 1790.

According to United Kingdom Prospective Diabetes Study (UKPDS) (Clarke et al. Diabetologia, 2005, 48, 868-877), metformin therapy was cost-saving and increased quality-adjusted life expectancy. In the UKPDS, overweight and obese patients randomized to initial therapy with metformin experienced significant reductions in myocardial infarction and diabetes-related deaths. Metformin does not promote weight gain and has beneficial effects on several cardiovascular risk factors. Accordingly, metformin is widely regarded as the drug of choice for most patients with type 2 diabetes. However, even diabetic patients on metformin therapy face the risk of long-term cardiovascular complications such as cardiac arrhythmia, cardiac ischemia, myocardial infarction, cardiomyopathy and stroke. It is thought that elevated triglycerides (TGs) may be an important common biochemical link underpinning the cardiovascular complications. Epidemiological and clinical evidence suggests that an increased intake of ω-3 polyunsaturated fatty acids (PUFAs) protects against mortality from coronary artery diseases. PUFAs include eicosapentaenoic acid (EPA) and docosahexaenoic acid (DHA). It is widely established that PUFAs protect against and can terminate ischemic ventricular arrhythmias (Billman et al. Circulation. 1999, 99, 2452-2457 and Kang et al. Am. J. Clin. Nutr. 2002, 71, 202S-207S). In particular, it is known that EPA is a promising treatment for prevention of major coronary events. PUFAs have multiple biological functions through lipid-dependent and lipid-independent mechanisms. EPA and mixtures of EPA and DHA have been shown to ameliorate triglycerides (TGs) lipid levels in patients with very high TGs. Also, EPA is shown to increase adiponectin secretion both in obese animals and obese human subjects (Itoh et al. Arteroscler. Thromb. Vasc. Biol. 2007, 27, 1918-1925). Increased adiponectin levels are beneficial in regulating both lipid and glucose metabolism in animals as well as in humans. It is also known that many patients with type 2 diabetes and with a prediabetic condition known as metabolic syndrome, sometimes referred to as insulin resistance, suffer from a variety of glucose and lipid metabolism disorders including elevated blood glucose and triglycerides.

Accordingly, provided herein are compounds of Formula I, as well as methods for treating diabetes, diabetes with concomitant dyslipidemia (e.g., high triglycerides) and diabetes exacerbated cardiovascular complications, such as cardiac arrhythmia, cardiac ischemia, myocardial infarction, cardiomyopathy, and stroke, comprising administering to a subject in need thereof a compound of Formula I. Compounds of Formula I are also useful in treating obesity in a subject in need thereof.

Compounds of Formula I are tri-salts of a compound having two acidic and one basic functional groups, metformin, and a polyunsaturated fatty acid, and are represented by the following formula:

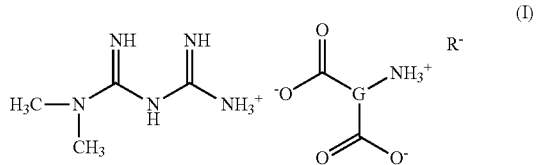
(I)

-continued

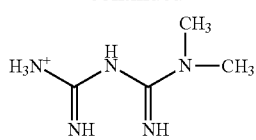

wherein G is an alkyl, cycloalkyl, heteroalkyl, heterocyclyl, aryl, or heteroaryl group; and R$^-$ is a polyunsaturated fatty acid. In an embodiment of Formula I, G is alkyl. When G is alkyl, G can be alkylene, e.g., $CH_2$, $CH_2CH_2$, $CH_2CH_2CH_2$, $CH_2CH_2CH_2CH_2$, $CH_2CH_2CH_2CH_2CH_2$, etc., wherein one of the hydrogens is replaced with the $NH_3^+$ depicted in Formula I.

In one embodiment, compounds of Formula I are represented by Formula II:

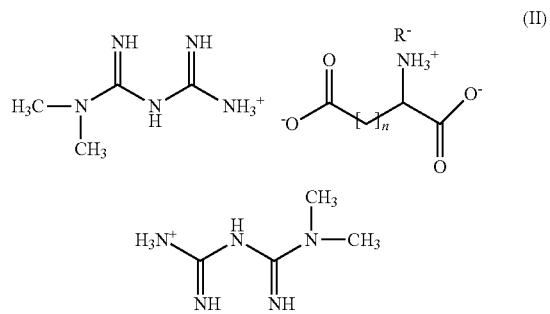
(II)

wherein n is 1-10, and R$^-$ is a polyunsaturated fatty acid. In a particular embodiment of Formula II, n is 1-2. In another particular embodiment of Formula II, n is 3-5.

In an embodiment of Formula II, R$^-$ is eicosapentaenoate:

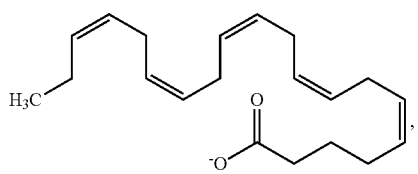

or docosahexaenoate:

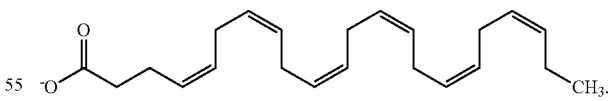

In one embodiment of Formula II, R$^-$ is eicosapentaenoate, and n is 1. In another embodiment of Formula II, R$^-$ is eicosapentaenoate and n is 2.

In another embodiment of Formula II, R$^-$ is docosahexaenoate and n is 1. In another embodiment of Formula II, R$^-$ is docosahexaenoate and n is 2.

In certain embodiments, the compound of Formula II is selected from the group consisting of Compounds A, B, C, D, E, F, G, H, I, and J:

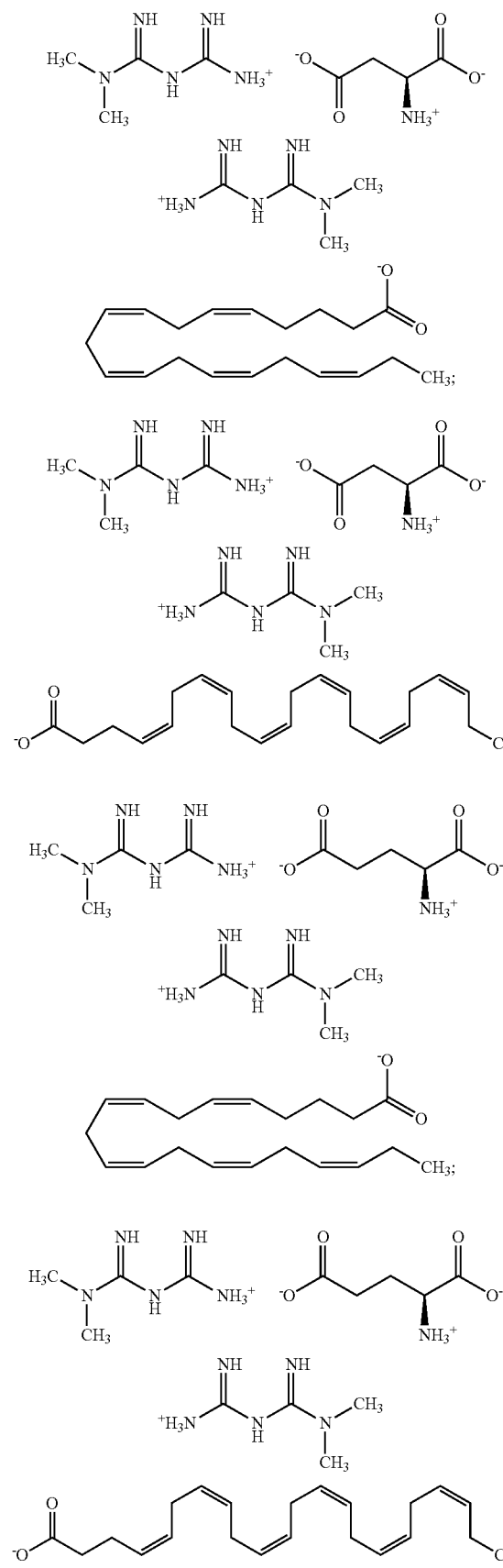
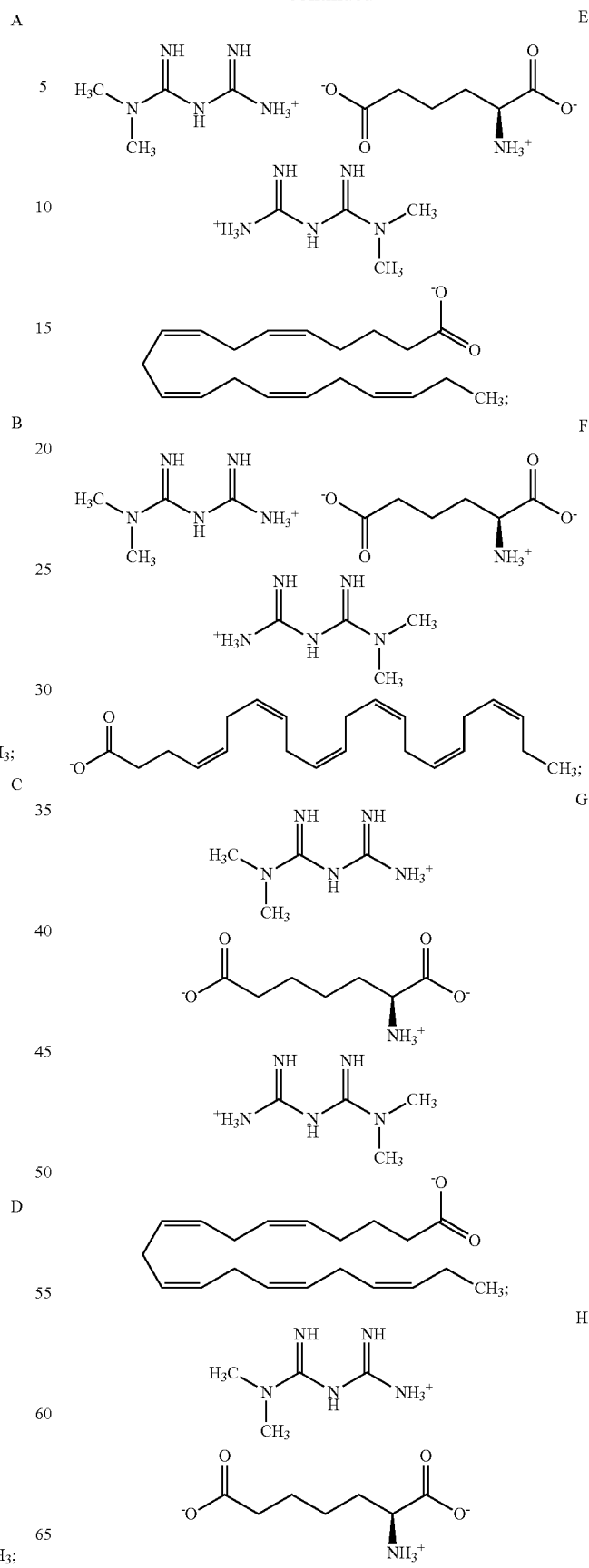

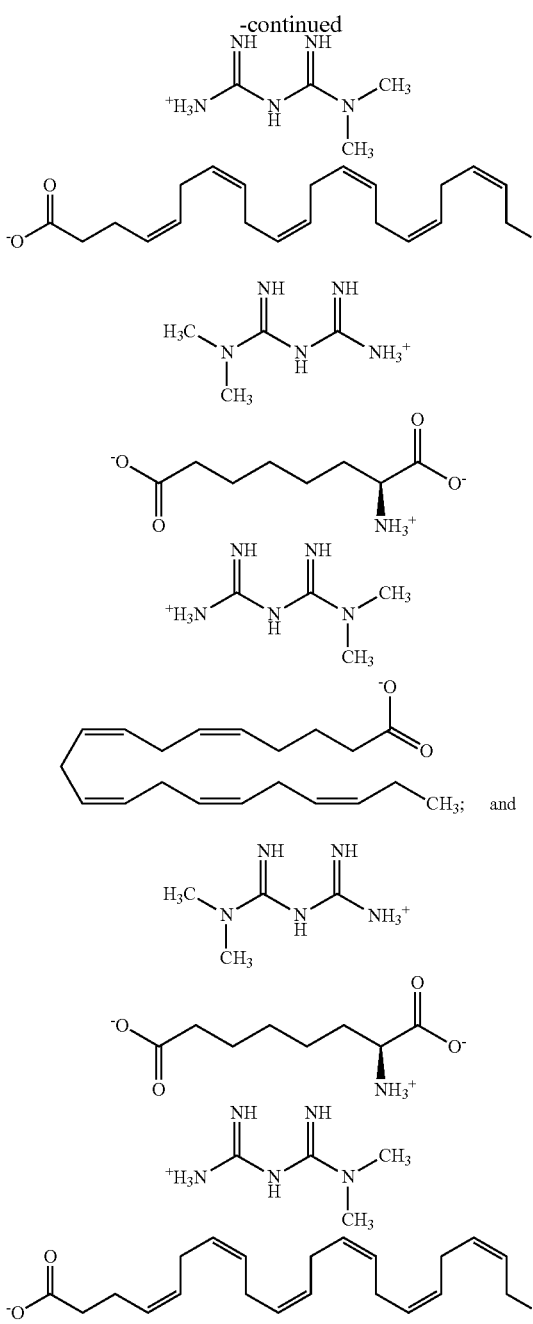

The compounds of Formula I also include isomers and enantiomers wherever it is applicable.

It is well known in the art that highly water soluble medicinal preparations, when administered orally, result in efficient absorption of such preparations from the gastrointestinal tract into systemic circulation. Another hallmark of such preparations is the rate at which they are absorbed into systemic circulation resulting in high concentration of the active agent or agents in the blood. Moreover, for delivery of xenobiotics via the intravenous route, they must be presented as a clear solution. PUFAs and esters of PUFAs are practically insoluble in water. In fact, they form soap-like emulsions when mixed with water. Therefore, the potential to achieve optimum therapeutic benefits of PUFAs should be markedly facilitated by delivery of water soluble PUFAs. The compounds of the present invention are markedly more water soluble than PUFAs and esters of PUFAs to achieve high oral absorption and to provide concomitant delivery of both metformin and PUFAS, thus providing a dual action in targeting both elevated blood glucose levels and TGs prevalent in type 2 diabetes in patients. Furthermore, the new salts would offer a patient friendly dosage form of two active therapies in a fixed dosage combination with increased reliability for daily patient compliance. Juvisync, recently approved by the United States Food and Drug Administration, is a contemporary example of a fixed combination of two widely used drugs for reliability of usage and patient convenience (FDA News Release. Oct. 7, 2011). Furthermore, the compounds of the present invention enable the preparation of intravenous dosage forms.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, 1 to 6 carbons, 1 to 4 carbons, or 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. As used herein, the term "alkyl" also includes "alkenyl" and "alkynyl" groups.

The term "alkenyl," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "alkynyl" includes unsaturated aliphatic groups analogous in length to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

As used herein, the term "cycloalkyl" refers to saturated or unsaturated monocyclic, bicyclic or tricyclic hydrocarbon groups of 3 to 12 carbon atoms, preferably 3 to 9, or 3 to 7 carbon atoms. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like. As used herein, "cycloalkyl" includes "cycloalkenyl" groups.

The term "cycloalkenyl" refers to a partially unsaturated cyclic hydrocarbon group containing 1 to 3 rings and 4 to 8 carbons per ring. Exemplary groups include cyclobutenyl, cyclopentenyl, and cyclohexenyl. The term "cycloalkenyl"

also includes bicyclic and tricyclic groups in which at least one of the rings is a partially unsaturated, carbon-containing ring and the second or third ring may be carbocyclic or heterocyclic, provided that the point of attachment is to the cycloalkenyl group.

The term "heteroalkyl," by itself or in combination with another term, means, unless otherwise stated, a stable straight or branched chain, or combinations thereof, consisting of the stated number of carbon atoms and from 1 to 5 heteroatoms, more preferably from 1 to 3 heteroatoms, selected from the group consisting of O, N, Si and S, and wherein the nitrogen and sulfur atoms may optionally be oxidized and the nitrogen heteroatom may optionally be quaternized. The heteroalkyl group is attached to the remainder of the molecule through a carbon atom or a heteroatom.

The term "aryl" includes aromatic monocyclic or multicyclic e.g., tricyclic, bicyclic, hydrocarbon ring systems consisting only of hydrogen and carbon and containing from 6 to 19 carbon atoms, or 6 to 10 carbon atoms, where the ring systems may be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" refers to a five-member to ten-member, fully saturated or partially unsaturated nonaromatic heterocyclic groups containing at least one heteroatom such as O, S or N. The most frequent examples are piperidinyl, morpholinyl, piperazinyl, pyrrolidinyl or pyrazinyl. Attachment of a heterocyclyl substituent can occur via a carbon atom or via a heteroatom.

Moreover, the alkyl, heteroalkyl, cycloalkyl, aryl, heteroaryl, and heterocycle groups described above can be "unsubstituted" or "substituted." The term "substituted" is intended to describe moieties having substituents replacing a hydrogen on one or more atoms, e.g. C, O or N, of a molecule. Such substituents can independently include, for example, one or more of the following: straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}$ NR'R'' (e.g., —$NH_2$), $(CR'R'')_{0-3}$ CN (e.g., —CN), —$NO_2$, halogen (e.g., —F, —Cl, —Br, or —I), $(CR'R'')_{0-3}$C(halogen)$_3$ (e.g., —$CF_3$), $(CR'R'')_{0-3}$CH(halogen)$_2$, $(CR'R'')_{0-3}$CH$_2$(halogen), $(CR'R'')_{0-3}$CONR'R''$, $(CR'R'')_{0-3}$(CNH)NR'R'', $(CR'R'')_{0-3}$S(O)$_{1-2}$NR'R''$, $(CR'R'')_{0-3}$CHO, $(CR'R'')_{0-3}$O$(CR'R'')_{0-3}$H, $(CR'R'')_{0-3}$S(O)$_{0-3}$R'$ (e.g., —$SO_3H$, —$OSO_3H$), $(CR'R'')_{0-3}$O$(CR'R'')_{0-3}$H (e.g., —$CH_2OCH_3$ and —$OCH_3$), $(CR'R'')_{0-3}$S$(CR'R'')_{0-3}$H (e.g., —SH and —$SCH_3$), $(CR'R'')_{0-3}$OH (e.g., —OH), $(CR'R'')_{0-3}$COR'$, $(CR'R'')_{0-3}$ (substituted or unsubstituted phenyl), $(CR'R'')_{0-3}$ ($C_3$-$C_8$ cycloalkyl), $(CR'R'')_{0-3}$CO$_2$R'$ (e.g., —$CO_2H$), or $(CR'R'')_{0-3}$OR'$ group, or the side chain of any naturally occurring amino acid; wherein R' and R'' are each independently hydrogen, a $C_1$-$C_5$ alkyl, $C_2$-$C_5$ alkenyl, $C_2$-$C_5$ alkynyl, or aryl group.

Methods of Treatment

Provided herein is a tri-salt having the Formula I. In other embodiments provided herein is a tri-salt having the Formula II. In certain embodiments, the compound of Formula II is selected from the group consisting of Compounds A, B, C, D, E, F, G, H, I, and J.

These compounds are effective for the treatment of T2D, pre-diabetes, obesity, metabolic syndrome, hypertriglyceridemia and T2D complications such as neuropathy, nephropathy, retinopathy, cataracts and cardiovascular complications, including cardiac arrhythmia, myocardial infarction, stroke, and cardiomyopathy in diabetic patients.

Diabetes mellitus, commonly called diabetes, refers to a disease process derived from multiple causative factors and characterized by elevated levels of plasma glucose, referred to as hyperglycemia. See, e.g., LeRoith, D. et al., (eds.), Diabetes Mellitus (Lippincott-Raven Publishers, Philadelphia, Pa. U.S.A. 1996). Uncontrolled hyperglycemia is associated with increased and premature mortality due to an increased risk for macrovascular and macrovascular diseases, including nephropathy, neuropathy, retinopathy, hypertension, cerebrovascular disease and coronary heart disease.

There are two major forms of diabetes: type 1 diabetes (formerly referred to as insulin-dependent diabetes or IDEM); and type 2 diabetes (formerly referred to as noninsulin dependent diabetes or NIDDM).

Type 2 diabetes (T2D) is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In type 2 diabetes, free fatty acid levels are often elevated in obese and some non-obese patients and lipid oxidation is increased.

The term "obesity" is defined as the condition wherein the individual has a BMI equal to or greater than 30 kg/m$^2$. According to a WHO definition the term obesity may be categorized as follows: the term "class I obesity" is the condition wherein the BMI is equal to or greater than 30 kg/m$^2$ but lower than 35 kg/m$^2$; the term "class II obesity" is the condition wherein the BMI is equal to or greater than 35 kg/m² but lower than 40 kg/m²; the term "class III obesity" is the condition wherein the BMI is equal to or greater than 40 kg/m².

The term "euglycemia" is defined as the condition in which a subject has a fasting blood glucose concentration within the normal range, greater than 70 mg/dL (3.89 mmol/L) and less than 100 mg/dL (5.6 mmol/L). The word "fasting" has the usual meaning as a medical term.

The term "hyperglycemia" is defined as the condition in which a subject has a fasting blood glucose concentration above the normal range, greater than 100 mg/dL (5.6 mmol/L). The word "fasting" has the usual meaning as a medical term.

The term "impaired glucose tolerance" or "IGT" is defined as the condition in which a subject has a 2 hour postprandial blood glucose or serum glucose concentration greater than 140 mg/di (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dL (7.78 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-tohip ratio <1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. *JAMA*. (2002) 287:356-9). A method of determining insulin resistance is the euglycaemichyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance. Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., *Diabetologia* 1985, 28:412-19), of the ratio of intact proinsulin to insulin (Forst et al., *Diabetes* 2003, 52(Suppl.1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P., et al. Diabet. Med. 1992; 9:921-8):HOMA-IR=[fasting serum insulin(uU/mUx[fasting plasma glueose(nunol/L)/22.5]

As a rule, other parameters are used in everyday clinical practice to assess insulin resistance. Preferably, the patient's triglyceride concentration is used, for example, as increased triglyceride levels correlate significantly with the presence of insulin resistance.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am. J. Epidemiol.* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference>40 inches or 102 cm in men, and >35 inches or 94 cm in women; or with regard to a Japanese ethnicity or Japanese patients defined as waist circumference of 85 cm in men and 90 cm in women;
2. Triglycerides: ⁻150 mg/dL
3. HDL-cholesterol<40 mg/dL in men
4. Blood pressure: 130/85 mm Hg (SBP130 or DBP85)
5. Fasting blood glucose: ⁻100 mg/dL Patients with a predisposition for the development of IGT or IFG or T2D are those having euglycemia with hyperinsulinemia and are by definition, insulin resistant. A typical patient with insulin resistance is usually overweight or obese. If insulin resistance can be detected, this is a particularly strong indication of the presence of pre-diabetes.

Thus, it may be that in order to maintain glucose homoeostasis a person needs 2-3 times as much insulin as a healthy person, without this resulting in any clinical symptoms.

The methods to investigate the function of pancreatic beta-cells are similar to the above methods with regard to insulin sensitivity, hyperinsulinemia or insulin resistance: An improvement of beta-cell function can be measured for example by determining a HOMA-index for beta-cell function (Matthews et al., *Diabetologia* 1985, 28:412-19), the ratio of intact proinsulin to insulin (Forst et al., *Diabetes* 2003, 52(Suppl.1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur. J. Clin. Invest.* 2001, 31: 38081).

"Pre-diabetes" is the condition wherein an individual is pre-disposed to the development of type 2 diabetes. Pre-diabetes extends the definition of impaired glucose tolerance to include individuals with a fasting blood glucose within the high normal range 100 mg/dL (J. B. Meigs, et al. Diabetes 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

Individuals likely to have insulin resistance are those who have two or more of the following attributes: 1) overweight or obese, 2) high blood pressure, 3) hyperlipidemia, 4) one or more 1 degree relative with a diagnosis of IGT or IFG or type 2 diabetes. Insulin resistance can be confirmed in these individuals by calculating the HOMA-IR score. For the purpose of this invention, insulin resistance is defined as the clinical condition in which an individual has a HOMA-IR score>4.0 or a HOMA-IR score above the upper limit of normal as defined for the laboratory performing the glucose and insulin assays.

The term "type 2 diabetes" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/1) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage T2D mellitus" includes patients with a secondary drug failure, indication for insulin therapy and progression to micro- and macrovascular complications e.g. diabetic nephropathy, or coronary heart disease (CHD)

The methods, compositions, and kits of the invention are useful in treating diabetic complications, including, but not limited to, diabetic neuropathy, diabetic nephropathy, diabetic cardiomyopathy, myocardial infarction, cataracts and diabetic retinopathy.

The term "treating," as used herein, refers to retarding, arresting, or reversing the progress of, or alleviating or preventing either the disorder or condition to which the term "treating", applies, or one or more symptoms of such disorder or condition.

The term "treatment," as used herein, refers to the act of treating a disorder, symptom, or condition, as the term "treating," is defined above.

The triglyceride lowering efficacy of the compounds of the present invention can be determined in animal models according to the procedure described by Sidika et al. in Journal of Lipid Research, 1992, 33, 1-7.

In still another aspect, provided herein is a method of treating atherosclerosis, comprising administering to a subject in need thereof an effective amount of a compound of the invention. Atherosclerosis refers to the buildup of fats and cholesterol in and on artery walls (plaques), which can restrict blood flow. These plaques can also burst, triggering a blood clot. Although atherosclerosis is often considered a heart problem, it can affect arteries anywhere in the body. An animal model of atherosclerosis research is described in *Laboratory Animals* (2004) 38, 246-256.

In another embodiment, compounds of Formula I (e.g., compounds of Formula II and Compounds A, B, C, D, E, F, G, H, I, and J) can be administered in combination with additional forms of metformin. For example, compounds of Formula I can be administered to a subject in combination with metformin docosahexaenoate, metformin eicosapentaenoate, or a mixture thereof. In another embodiment, compounds of Formula I can be administered in combination with a nonfatty acid salt form of metformin, e.g., metformin hydrochloride, succinate, or fumarate, or in combination with the free base of metformin Metformin hydrochloride can be purchased commercially and can also be prepared, for example, as disclosed in J. Chem. Soc., 1922, 121, 1790.

In addition, compounds of Formula I can be administered in combination with eicosapentanoic acid, and/or docosahexaenoic acid.

Combination Therapy

The tri-salts of the present invention are well-suited to use in combination therapy.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate containers (e.g., capsules) for each active ingredient. In addition, such administration also encompasses use of each type of therapeutic agent in a sequential manner, either at approximately the same time or at different times. In either case, the treatment regimen will provide beneficial effects of the drug combination in treating the conditions or disorders described herein.

The term "single formulation" as used herein refers to a single carrier or vehicle formulated to deliver effective amounts of both therapeutic agents to a patient. The single vehicle is designed to deliver an effective amount of each of the agents, along with any pharmaceutically acceptable carriers or excipients. In some embodiments, the vehicle is a tablet, capsule, pill, or a patch. In other embodiments, the vehicle is a solution or a suspension.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents along with pharmaceutically acceptable carriers and excipients. In some embodiments, the unit dose is one or more tablets, capsules, pills, or patches administered to the patient at the same time.

An "oral dosage form" includes a unit dosage form prescribed or intended for oral administration.

A "mixture of compounds of Formula I or II" refers to a mixture of two or more of these compounds present in a and b %, wherein a and b are not zero, but the sum of a and b is 100%. For example, when a compound is made up of a mixture of a compound of Formula I and a compound of Formula II, a compound of Formula I is present at 50% and a compound of Formula II is present at 50%.

In one embodiment, provided herein is a combination therapy comprising an effective amount of a compound of Formula I or II, or a combination thereof, and an antihyperlipidemic agent or an antihyperglycemic agent. An "effective amount" of a combination of agents is an amount sufficient to provide an observable improvement over the baseline clinically observable signs and symptoms of the disorders treated with the combination.

In one embodiment, the combination of a compound of Formula I or II, or a combination thereof, and an antihyperlipidemic agent or an antihyperglycemic agent described herein displays a synergistic effect. The term "synergistic effect" as used herein, refers to action of two agents producing an effect, for example, slowing the symptomatic progression of diabetes or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)) incorporated by reference, herein, in its entirety, the equation of Loewe additivity (Loewe, S. and Muischnek, H., Arch. Exp. Pathol Pharmacol. 114: 313-326 (1926)) incorporated by reference, herein, in its entirety, and the median-effect equation (Chou, T. C. and Talalay, P., Adv. Enzyme Regul. 22: 27-55 (1984)) incorporated by reference, herein, in its entirety. Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The expression "pharmaceutically acceptable salts" includes both pharmaceutically acceptable acid addition salts and pharmaceutically acceptable cationic salts, where appropriate. The expression "pharmaceutically-acceptable cationic salts" is intended to define but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzyl phenethylamine), diethylamine, piperazine, tromethamine(2-amino-2-hydroxymethyl-1,3-propanediol) and procaine.

The expression "pharmaceutically-acceptable acid addition salts" is intended to define but is not limited to such salts as those with pharmaceutically acceptable mineral or organic acids classically used in pharmacy. Appropriate acids are, for example, inorganic acids, such as hydrohalic acid, e.g. hydrochloric, hydrobromic or the like, or sulfuric acid, nitric acid, or phosphoric acid; or suitable organic acids, for example suitable aliphatic acids, like aliphatic mono or dicarboxylic acids, hydroxyalkanoic or hydroxyalkanedioic acids, e.g. acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, or 2-hydroxy-1,2,3-propanetricarboxylic acid; phenyl substituted alkanoic acids; or suitable aromatic acids, like 2-hydroxybenzoic, or 4-amino-2-hydroxybenzoic acid; or suitable sulfonic acids, like alkanesulfonic acids, e.g. methanesulfonic, or ethanesulfonic acid, or aromatic sulfonic acids, e.g. benzenesulfonic, or 4-methylbenzenesulfonic acid; or cyclohexanesulfamic acid. In certain embodiments of the disclosure, acids are e.g. hydrobromic acid, sulphuric acid, phosphoric acid, acetic, benzoic, fumaric, maleic, citric, tartaric, gentisic, dobesilic, methanesulfonic, ethanesulfonic, laurylsulfonic, benzenesulfonic, and para-toluenesulfonic acids. In certain embodiments, the pharmaceutically acceptable salt is selected from the group consisting of an L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium hydroxide, L-lysine, magnesium hydroxide, 4-(2-hydroxyethyl)morpholine, piperazine, potassium hydroxide, 1-(2-hydroxyethyl)pyrrolidine, sodium hydroxide, triethanolamine, tromethamine, zinc hydroxide, sodium, calcium, potassium, magnesium, and zinc.

Combination Therapy with Antihyperlipidemic Agents

In another aspect, provided herein is a combination therapy comprising a compound of the structural Formula I or II above, and an antihyperlipidemic agent, to treat a metabolic disorder selected from the group consisting of T2D, prediabetes, obesity, metabolic syndrome, hypertriglyceridemia and T2D complications such as neuropathy, nephropathy, retinopathy, cataracts and cardiovascular complications, including atrial fibrillation, cardiac arrhythmia, myocardial infarction, stroke, and cardiomyopathy in mammals, e.g., diabetic patients. An additional aspect provided herein is combination therapy comprising a compound of the structural Formula I or II and an antihyperlipidemic agent, to treat obesity, cardiovascular disease, and related indications in a subject in need thereof.

In another embodiment, provided herein is a method of lowering the cholesterol level and/or the triglyceride level in a mammal comprising administering to the mammal an effective amount of the combination therapy of the invention.

Accordingly, in one aspect, provided herein is a method for treating diabetes in a subject in need thereof, comprising administering to the subject a therapeutically effective amount of the combination therapy described above. In another aspect, provided herein is a method of lowering triglycerides in a subject in need thereof, comprising administering to a subject in need thereof an effective amount of the combination therapy of the invention. In still another aspect, provided herein is a method for treating cardiovascular diseases in a subject in need thereof, administering to a subject in need thereof an effective amount of the combination therapy of the invention. Examples of cardiovascular diseases to be treated are cardiac arrhythmia, cardiac ischemia, myocardial infarction, cardiomyopathy, or stroke.

In another aspect, provided herein is a method for treating obesity in a subject in need thereof, administering to a subject in need thereof an effective amount of the combination therapy of the invention.

In one aspect, provided herein is a method of treating hyperlipidemia, administering to a subject in need thereof an effective amount of the combination therapy of the invention. In another aspect, provided herein is a method of treating hypertriglyceridemia, administering to a subject in need thereof an effective amount of the combination therapy of the invention. In another aspect, provided herein is a method of treating dyslipidemia, administering to a subject in need thereof an effective amount of the combination therapy of the invention.

In another aspect, provided herein is a method of treating prediabetes, administering to a subject in need thereof an effective amount of the combination therapy of the invention.

In still another aspect, provided herein is a method of treating atherosclerosis, administering to a subject in need thereof an effective amount of the combination therapy of the invention.

In one embodiment of the above methods, the subject is human.

In one aspect, the invention relates to a combination therapy comprising a compound of the structural Formula I or II or a compound of the structural Formula I or II and an antihyperlipidemic agent, or a combination of two or more compounds of the structural Formulas I or II or a compound of the structural Formula I or II and an antihyperlipidemic agent and a pharmaceutically-acceptable salt or prodrug thereof, or a pharmaceutically-acceptable salt of said prodrug. In another aspect, provided herein is a pharmaceutical composition comprising a compound of the structural Formula I or II, or a mixture of these, an antihyperlipidemic agent and a pharmaceutically-acceptable carrier. In one embodiment, when the pharmaceutical composition comprises two or more compounds of the structural Formula I or II, or a mixture of these, the two or more compounds are present in x, y, z, . . . % etc. with the proviso that x, y, z, . . . % are not zero, but the sum x, y, z, . . . % is 100%.

In one embodiment of the pharmaceutical composition, the antihyperlipidemic agent is about 0.1-1% by weight of the pharmaceutical composition. In another embodiment of the pharmaceutical composition, the compound of the structural Formula I or II, or a mixture thereof is present in unit dosage strength of 250, 500, 750, 1000 or 1250 mg, and the said antihyperlipidemic agent is present in a unit dosage strength of 1, 2.5, 5, 10, 20, 30, 40, or 50 mg. In another embodiment, the said antihyperlipidemic agent is present in a unit dosage strength of 5-100 mg.

The components of the combination therapy (a compound of the structural Formula I or II and an antihyperlipidemic agent, or a combination of two or more compounds of the structural Formulas I or II and an antihyperlipidemic agent) can be administered in a variety of ways. In one embodiment, the components are in separate formulations or unit dosage forms. In another embodiment, the components are administered with a pharmaceutically acceptable carrier. The components can be administered separately, at substantially the same time, or administered at different times. When administered separately, they can be administered in any order.

In one embodiment, the present invention is directed to pharmaceutical compositions comprising compound of the structural Formula I or II, or a mixture of these and an antihyperlipidemic agent, or a pharmaceutically-acceptable salt or prodrug thereof, or a pharmaceutically-acceptable salt of said prodrug; and a pharmaceutically-acceptable carrier, vehicle or diluent.

Antihyperlipidemic agents that may be used in accordance with the invention may include, for example, statins, which are HMG CoA enzyme inhibitors, cholesterol absorption inhibitors, and cholesterol esterase transfer protein (CETP) inhibitors and pharmaceutically-acceptable salts and prodrug thereof, and pharmaceutically-acceptable salts of said prodrug, and others.

In one embodiment of the present invention, the antihyperlipidemic agent is a statin, cholesterol absorption inhibitor, and CETP inhibitor or a pharmaceutically-acceptable salt or prodrug thereof, or a pharmaceutically-acceptable salt of said prodrug. In certain embodiments the pharmaceutically acceptable salt is selected from the group consisting of a propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenyl acetate, phenylpropionate, phenylbutyrate, citrate, lactate, p-hydroxybutyrate, glycolate, tartrate, methanesulfonate, propanesulfonates, naphthalene-1-sulfonate, naphthalene-2-sulfonate, mandelate, hippurate, gluconate, or lactobionate.

Preferred agents among statins are atorvastatin, risuvostatin, simvastatin, or pravastatin, pharmaceutically-acceptable salts or a prodrugs thereof, and pharmaceutically-acceptable salts of said prodrugs. Preferred agents among cholesterol absorption inhibitors is ezetimibe also known as Zetia. Preferred agents among CETP inhibitors is anacetrapib. In certain embodiments, CETP inhibitors include, but are not limited to anacetrapib or a hydrate, and solvate thereof.

In certain embodiments, the pravastatin is present in the amount ranging from 5 mg to 100 mg.

In certain embodiments, the ezetimibe is present 5 mg to 50 mg.

In another aspect, the disclosure provides for kits comprising a first unit dosage form comprising compound of the structural Formula I or II, or a mixture of these; a second unit dosage form comprising an antihyperlipidemic agent or a hydrate, and solvate thereof; and a container.

In one embodiment of the antihyperlipidemic therapy described herein, G is an alkyl, cycloalkyl, heteroalkyl, heterocyclyl, aryl, or heteroaryl group; and $R^-$ is a polyunsaturated fatty acid. In an embodiment of Formula I, G is alkyl. When G is alkyl, G can be alkylene, e.g., $CH_2$, $CH_2CH_2$, $CH_2CH_2CH_2$, $CH_2CH_2CH_2CH_2$, $CH_2CH_2CH_2CH_2CH_2$, etc., wherein one of the hydrogens is replaced with the $NH_3^+$ depicted in Formula I.

In a particular embodiment, compounds of Formula I are of the Formula II, wherein $R^-$ is a polyunsaturated fatty acid, and n is 1-10, or a pharmaceutically acceptable solvate or hydrate thereof. In a particular embodiment of Formula II, n is 1 or 2. In an embodiment of Formulas I and II, $R^-$ is eicosapentaenoate or docosahexaenoate. In an embodiment of Formula II, $R^-$ is eicosapentaenoate or docosahexaenoate, and n is 1. In still another embodiment of Formula II, $R^-$ is eicosapentaenoate or docosahexaenoate, and n is 2. In still further embodiments, the compounds of Formula II are selected from the group consisting of Compounds A, B, C, D, E, F, G, H, I, and J.

The antihyperlipidemic agents that may be used in accordance with the invention are members of different classes of antihyperlipidemic agents (e.g., HMG-CoA reductase inhibitors (statins), CETP inhibitors, and cholesterol absorption inhibitors and others), pharmaceutically-acceptable salts and prodrugs thereof, and pharmaceutically-acceptable salts of said prodrugs.

The term "HMG-CoA reductase inhibitor" as used herein refers to a compound that competitively blocks the enzyme 3-hydroxy-3-methyl-glutaryl-co-enzyme A (HMG-CoA) reductase. By competitively blocking this enzyme, the HMG-CoA reductase inhibitors interfere with cholesterol formation (enzyme catalyzes the conversion of HMG-CoA to mevalonate). As a result, they decrease total cholesterol, low-density lipoprotein cholesterol (LDL-C), apolipoprotein B (a membrane transport complex for LDL-C), very low-density lipoprotein (VLDL), and plasma triglycerides. For a review on HMG-CoA inhibitors see, for example, *Drug Discovery Today: Therapeutic Strategies*, 1:189 (2004) and references cited therein.

The specific HMG-CoA reductase inhibitors which may be used in accordance with the disclosure include, but are not limited to: atorvastatin, which may be prepared as disclosed in U.S. Pat. No. 7,030,151; pravastatin and related compounds which may be prepared as disclosed in U.S. Pat. Nos. 4,346,227 and 4,448,979; rosuvastatin, which may be prepared as disclosed in U.S. Pat. No. 6,858,618; simvastatin and related compounds which may be prepared as disclosed in U.S. Pat. Nos. 4,448,784 and 4,450,171. HMG-CoA reductase inhibitors also include atorvastatin, simvastatin, pravastatin, lovastatin, fluvastatin, rosuvastatin, cerivastatin, mevastatin, rivastatin, pitavastatin, nisvastatin, itavastatin, velostatin and fluindostatin.

The term "CETP inhibitor" as used herein refers to a compound which catalyses the transfer of cholesteryl ester from HDL to apolipoprotein B containing lipoproteins in exchange for triglyceride and thereby plays a major role in lipoprotein metabolism. For a review on CETP inhibitors see, for example, *Curr. Opin. Pharmacol.* 6:162 (2006) and references cited therein.

CETP inhibitors which may be used in accordance with the disclosure are not limited by any structure or group of CETP inhibitors. CETP inhibitors which may be used in accordance with the disclosure include, but are not limited to: anacetrapib, which may be prepared as disclosed in WO 2007005572. The disclosure thereof is incorporated herein by reference.

The term "cholesterol absorption inhibitors" as used herein refers to a compound that inhibits the absorption of biliary and dietary cholesterol from the small intestine without affecting the absorption of fat-soluble vitamins, triglycerides, or bile acids. For a review on cholesterol absorption inhibitors see, for example, *Nutr. Metab. Cardiovasc. Dis.*, 13:42 (2004) and references cited therein.

Cholesterol absorption inhibitors which may be used in accordance with the disclosure include, but are not limited to ezetimibe (Zetia), which may be prepared as disclosed in U.S. Pat. Nos. 5,767,115 and 5,846,966. The disclosures thereof are incorporated herein by reference.

In the practice of the compositions and methods of the disclosure, any HMG Co-A reductase inhibitors (or) or in a pharmaceutically acceptable combination with any flushing inhibiting agent may be employed.

In one aspect, the disclosure provides for pharmaceutical compositions comprising a compound of Formula I or II, or a mixture thereof; and an antihyperlipidemic agent or a pharmaceutically acceptable salt, hydrate, and solvate thereof.

In one aspect, the disclosure provides for unit dose formulations comprising a compound of Formula I or II, or a mixture thereof, and an antihyperlipidemic agent or a pharmaceutically acceptable salt, hydrate, and solvate.

In one aspect, the disclosure provides for methods of treating a diabetic cardiovascular complication in a mammal comprising administering to said mammal a pharmaceutical composition as set forth herein below. In certain embodiments, such diabetic complications are, for example, atrial fibrillation, arrhythmia, myocardial infarction, stroke and cardiomyopathy.

In one aspect, the disclosure provides for methods of treating type 2 diabetes in a mammal comprising administering to said mammal a compound of Formula I or II, or a mixture thereof, and an antihyperlipidemic agent or a hydrate, and solvate hereof.

Accordingly, in one embodiment, provided herein are combination therapies comprising, at least, the following combination of agents:

1) a compound of Formula I and atorvastatin; a compound of Formula I and simvastatin; a compound of Formula I and pravastatin; a compound of Formula I and rosuvastatin; and a compound of Formula I and ezitimibe; a compound of Formula I and anacetrapib; a compound of Formula I and atorvastatin calcium;

2) a compound of Formula II and atorvastatin; a compound of Formula II and simvastatin; a compound of Formula II and pravastatin; a compound of Formula II and rosuvastatin; and a compound of Formula II and ezitimibe; a compound of Formula II and anacetrapib; a compound of Formula II and atorvastatin calcium.

In an additional embodiment, the combination therapies of paragraphs 1 and 2 above, can be further combined with compounds of Formula I and/or II.

Combination Therapy with Antihyperglycemic Agents

The present invention relates to a combination therapy comprising a compound of the structural Formula I or II above, and an antihyperglycemic agent, to treat a metabolic disorder selected from the group consisting of type 2 diabetes (T2D), pre-diabetes, obesity, metabolic syndrome, hypertriglyceridemia and T2D complications such as neuropathy, nephropathy, retinopathy, cataracts and cardiovascular complications, including cardiac arrhythmia, myocardial infarction, stroke, and cardiomyopathy in mammals, e.g., diabetic patients.

In one embodiment, the present invention provides a method of treating a metabolic disorder selected from the group consisting of T2D, pre-diabetes, obesity, metabolic syndrome, hypertriglyceridemia and diabetes complications such as neuropathy, nephropathy, retinopathy, cataracts and cardiovascular complications, including cardiac arrhythmia, myocardial infarction, and cardiomyopathy in mammals, e.g., diabetic patients, comprising administering to a subject in need thereof the combination therapy described herein The components of the combination therapy (a compound of the structural Formula I or II and an antihyperglycemic agent, or a combination of two or more compounds of the structural Formulas I or II and an antihyperglycemic agent) can be administered in a variety of ways. In one embodiment, the components are in separate formulations or unit dosage forms. In another embodiment, the components are administered with a pharmaceutically acceptable carrier. The components can be administered separately, at substantially the same time, or administered at different times. When administered separately, they can be administered in any order.

In one embodiment, the present invention is directed to pharmaceutical compositions comprising a compound of the structural Formula I or II, or a mixture of these, and an antihyperglycemic agent, or a pharmaceutically-acceptable salt or prodrug thereof, or a pharmaceutically-acceptable salt of said prodrug; and a pharmaceutically-acceptable carrier, vehicle or diluent.

In one embodiment of the pharmaceutical composition, the antihyperglycemic agent is about 1-20% by weight of the pharmaceutical composition. In another embodiment of the pharmaceutical composition, said compound of the structural Formula I or II, or a mixture thereof is present in unit dosage strength of 250, 500, 750, 1000 or 1250 mg, and the said antihyperglycemic agent is present in a unit dosage strength of 1, 2.5, 5, 10, 20, 25, 50, 100, 150, or 200 mg. In another embodiment, the antihyperglycemic agent is present in a unit dosage strength of 5-100 mg.

Antihyperglycemic agents that may be used in accordance with the invention may include, for example, sulfonylureas, meglitinides, thiazolidinediones, alpha-glucosidase inhibitors, DPP IV inhibitors, and SGLT-2 inhibitors and pharmaceutically-acceptable salts and prodrug thereof, and pharmaceutically-acceptable salts of said prodrug, and others.

In one embodiment of the present invention, the antihyperglycemic agent is a sulfonylurea, meglitinide, thiazolidinedione, alpha-glucosidase inhibitor, DPP IV inhibitor, and SGLT-2 inhibitors or a pharmaceutically-acceptable salt or prodrug thereof, or a pharmaceutically-acceptable salt of said prodrug. In certain embodiments the pharmaceutically acceptable salt is selected from the group consisting of a propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenyl acetate, phenylpropionate, phenylbutyrate, citrate, lactate, p-hydroxybutyrate, glycolate, tartrate, methanesulfonate, propanesulfonates, naphthalene-1-sulfonate, naphthalene-2-sulfonate, mandelate, hippurate, gluconate, or lactobionate.

Preferred agents among thiazolidinediones are pioglitazone, pharmaceutically-acceptable salts or a prodrugs thereof, and pharmaceutically-acceptable salts of said prodrugs.

Preferred alpha-glucosidase inhibitors include, but are not limited to, acarbose, vaglibose, and miglitol, pharmaceutically-acceptable salts and prodrugs thereof, and pharmaceutically-acceptable salts of said prodrugs.

Preferred DPP-IV inhibitors include, but are not limited to, sitagliptin, linagliptin, vildagliptin, saxagliptin, alogliptin, denagliptin, carmegliptin, melogliptin and dutogliptin. and pharmaceutically-acceptable salts and prodrugs thereof, and pharmaceutically-acceptable salts of said prodrugs.

Preferred SGLT-2 inhibitors include, but are not limited to, dapagliflozin canagliflozin, atigliflozin, remogliflozin and sergliflozin, and pharmaceutically-acceptable salts and prodrugs thereof, and pharmaceutically-acceptable salts of said prodrugs.

In one embodiment of the antihyperglycemic combination therapy described herein, G is an alkyl, cycloalkyl, heteroalkyl, heterocyclyl, aryl, or heteroaryl group; and $R^-$ is a polyunsaturated fatty acid. In an embodiment of Formula I, G is alkyl. When G is alkyl, G can be alkylene, e.g., $CH_2$, $CH_2CH_2$, $CH_2CH_2CH_2$, $CH_2CH_2CH_2CH_2$, $CH_2CH_2$ $CH_2CH_2CH_2$, etc., wherein one of the hydrogens is replaced with the $NH_3^+$ depicted in Formula I. In a particular embodiment, compounds of Formula I are of the Formula II wherein $R^-$ is a polyunsaturated fatty acid, and n is 1-10, or a pharmaceutically acceptable solvate or hydrate thereof. In a particular embodiment of Formula II, n is 1 or 2. In an embodiment of Formulas I and II, $R^-$ is eicosapentaenoate or docosahexaenoate. In an embodiment of Formula II, $R^-$ is eicosapentaenoate or docosahexaenoate, and n is 1. In still another embodiment of Formula II, $R^-$ is eicosapentaenoate or docosahexaenoate, and n is 2. In still further embodiments, the compounds of Formula II are selected from the group consisting of Compounds A, B, C, D, E, F, G, H, I, and J.

The antihyperglycemic agents that may be used in accordance with the invention are members of different classes of antihyperglycemic agents (e.g., sulfonylureas, meglitinides, thiazolidinediones, alpha-glucosidase inhibitors, DPP-IV inhibitors, SGLT-2 inhibitors and others), pharmaceutically-acceptable salts and prodrugs thereof, and pharmaceutically-acceptable salts of said prodrugs.

The term "sulfonylureas" refers to a class of compounds that stimulate insulin release by binding to the sulfonylurea receptor, a subunit of the ICATP channel complex. This binding leads to closure of the channel, resulting in voltage change in the beta-cell membrane and, in turn, influx of $Ca^{2+}$ ions causing exocytosis of insulin granules. For a discussion on sulfonylureas see, for example, *Metabolism*, 55, 20 (2006) incorporated by reference, herein, in its entirety and references cited therein, and *Lancet*, 358, 1709 (2001) incorporated by reference, herein, in its entirety and references cited therein.

The term "thiazolidinediones" refers to a class of compounds that are selective agonists for the peroxisome proliferator-activated receptor gamma (PPARγ), a member of family of nuclear hormone receptors that function as ligand-activated transcription factors. For a review on thiazolidinediones see, for example, *Trends Endocrin. Met.*, 10, 9 (1999) and references cited therein.

The term "alpha-glucosidase inhibitors" refers to a class of compounds having the ability to competitively inhibit brush border enzyme alpha-glucosidase in the GI tract, which has the ability to cleave complex carbohydrates into sugars. For a review on alpha-glucosidase inhibitors see, for example, Diabetes Res. Clin. Pr., 40, S51 (1998) and references cited therein.

The term "DPP IV inhibitors" refers to a class of compounds that have the ability to selectively inactivate the enzyme DPP-IV, and those which have the ability to rapidly inactivate incretin hormones (e.g., glucagon-like peptide-1 (GLP-1) and insulinotropic polypeptide (GIP)), that are released by the intestine throughout the day, and whose levels are increased after a meal. For a review on DPP-IV inhibitors see, for example, *Expert Opin. Inv. Drug*, 12, 87 (2003) and references cited therein. Specifically, the DPP-IV inhibitor sitagliptin can be prepared according to procedure described by Kim et al. in *Journal of Medicinal Chemistry*, 48, 141-151, (2005) and in *Journal of Medicinal Chemistry*, 51, 589-602, (2008).

The term "SGLT-2 inhibitors" refers to a class of compounds that have the ability to selectively inhibit renal sodium-glucose co-transporter 2 and prevent renal glucose reabsorption from the glomerular filtrate and provide an insulin-independent means of controlling hyperglycemia. For a perspective on SGLT-2 inhibitors see, for example, *Journal of Medicinal Chemistry*, 52, 1785 1794, (2009) and references cited therein.

In the practice of the compositions and methods of the invention, any sulfonylurea, meglitinide, thiazolidinedione, alpha-glucosidase inhibitor, DPP-1V inhibitor, or a SGLT-2 inhibitor or a pharmaceutically-acceptable salt or a prodrug thereof, or a pharmaceutically-acceptable salt of said prodrug, or any combination thereof, may be employed.

Sulfonylureas that may be used in accordance with the invention include, but are not limited to, acetohexamide, which may be prepared as described in U.S. Pat. No. 3,013, 072; 1-Butyl-3-methanilyl urea, which may be prepared as described in U.S. Pat. No. 3,183,260; carbutamide, which may be prepared as described in U.S. Pat. No. 4,324,796; chlorpropamide, which may be prepared as described in U.S. Pat. No. 4,381,304; glibornuride, which may be prepared as described in U.S. Pat. No. 4,153,710; gliclazide, which may be prepared as described in U.S. Pat. No. 6,733,782; glipizide, which may be prepared and its use as oral administration as described in U.S. Pat. No. 5,545,413; gliquidone, has been described and its use as described in U.S. Pat. No. 4,708,868; glyburide or glibenclamide, which may be prepared and its use as described in U.S. Pat. No. 6,830,760; glybuthiazole, which may be prepared as described in U.S. Pat. No. 7,144, 900; glybuzole, which may be prepared and its use as described in U.S. Pat. No. 7,084,123; glyhexamide, which may be described and its use as described in U.S. Pat. No. 5,859,037; glimepiride, which may be prepared and its use as described in U.S. Pat. No. 4,379,785; glymidine, which may be prepared and its use as described in U.S. Pat. No. 4,007, 201; tolazamide, which may be prepared as described in U.S. Pat. No. 3,583,979; tolbutamide, which may be prepared as described in U.S. Pat. No. 4,639,436. These patents are incorporated herein by reference.

The term "pioglitazone" as employed herein refers to pioglitazone, including its enantiomers, mixtures thereof and its racemate, or a pharmaceutically acceptable salt thereof such as the hydrochloride salt.

DPP-IV inhibitors that may be used in accordance with the invention include, but are not limited to, linagliptin, sitagliptin, vildagliptin, alogliptin, saxagliptin, denagliptin, carmegliptin, melogliptin, and dutogliptin, or a pharmaceutically-acceptable salt of one of the beforementioned DPP IV inhibitors, or a prodrug thereof.

The term "linagliptin" as employed herein refers to linagliptin and pharmaceutically acceptable salts thereof, including hydrates and solvates thereof, and crystalline forms thereof. Crystalline forms are described in WO 2007/128721. Methods for the manufacture of linagliptin are described in the patent applications WO 2004/018468 and WO 2006/048427 for example. Linagliptin is distinguished from structurally comparable DPP IV inhibitors, as it combines exceptional potency and a long-lasting effect with favorable pharmacological properties, receptor selectivity and a favorable side-effect profile or bring about unexpected therapeutic advantages or improvements when used in combination with an SGLT2 inhibitor and a third antidiabetic agent according to this invention.

The term "sitagliptin" as employed herein refers to sitagliptin (or MK-0431) and pharmaceutically acceptable salts thereof, including hydrates and solvates thereof, and crystalline forms thereof. In one embodiment, sitagliptin is in the form of its dihydrogenphosphate salt, i.e. sitagliptin phosphate. In a further embodiment, sitagliptin phosphate is in the form of a crystalline anhydrate or monohydrate. A class of this embodiment refers to sitagliptin phosphate monohydrate. Sitagliptin free base and pharmaceutically acceptable salts thereof are disclosed in U.S. Pat. No. 6,699,871 and in Example 7 of WO 03/004498. Crystalline sitagliptin phosphate monohydrate is disclosed in WO 2005/003135 and in WO 2007/050485. For details, e.g. on a process to manufacture or to formulate this compound or a salt thereof, reference is thus made to these documents. A tablet formulation for sitagliptin is commercially available under the trade name Januvia®.

The term "vildagliptin" as employed herein refers to vildagliptin (or LAF-237) and pharmaceutically acceptable salts thereof, including hydrates and solvates thereof, and crystalline forms thereof. Specific salts of vildagliptin are disclosed in WO 2007/019255. A crystalline form of vildagliptin as well as a vildagliptin tablet formulation are disclosed in WO 2006/078593. Vildagliptin can be formulated as described in WO 00/34241 or in WO 2005/067976. A modified release vildagliptin formulation is described in WO 2006/135723. For details, e.g. on a process to manufacture or to formulate this compound or a salt thereof, reference is thus made to these documents and U.S. Pat. No. 6,166,063. A tablet formulation for vildagliptin is expected to be commercially available under the trade name GALVUS®.

The term "saxagliptin" as employed herein refers to saxagliptin and pharmaceutically acceptable salts thereof, including hydrates and solvates thereof, and crystalline forms thereof In one embodiment, saxagliptin is in the form of the free base or a HCl salt (for example as mono- or dihydrochloride, including hydrates thereof), or a mono-benzoate salt as disclosed in WO 2004/052850 and WO 2008/131149. In a further embodiment, saxagliptin is in the form of the free base. In a yet further embodiment, saxagliptin is in the form of the monohydrate of the free base as disclosed in WO 2004/052850. A process for preparing saxagliptin is also disclosed in WO 2005/106011 and WO 2005/115982. Saxagliptin can be formulated in a tablet as described in WO 2005/117841. For details, e.g. on a process to manufacture, to formulate or to use this compound or a salt thereof, reference is thus made to these documents and U.S. Pat. No. 6,395,767 and WO 01/68603.

The term "denagliptin" as employed herein refers to denagliptin (or GSK-823093) and pharmaceutically acceptable salts thereof, including hydrates and solvates thereof, and crystalline forms thereof. In one embodiment, denagliptin is in the form of its hydrochloride salt as disclosed in Example 2 of WO 03/002531 or its tosylate salt as disclosed in WO 2005/009956. A class of this embodiment refers to denagliptin tosylate. Crystalline anhydrous denagliptin tosylate is disclosed in WO 2005/009956. For details on a process to manufacture this compound or a salt thereof, reference is thus made to these documents and to the U.S. Pat. No. 7,132,443.

The term "alogliptin" as employed herein refers to alogliptin (or SYR-322) and pharmaceutically acceptable salts thereof, including hydrates and solvates thereof, and crystalline forms thereof. In one embodiment, alogliptin is in the form of its benzoate salt, its hydrochloride salt or its tosylate salt each as disclosed in WO 2007/035629. A class of this embodiment refers to alogliptin benzoate. Polymorphs of alogliptin benzoate are disclosed in WO 2007/035372. A process for preparing alogliptin is disclosed in WO 2007/112368 and, specifically, in WO 2007/035629. Alogliptin (namely its benzoate salt) can be formulated in a tablet and administered as described in WO 2007/033266. For details, e.g. on a process to manufacture, to formulate or to use this compound or a salt thereof, reference is thus made to these documents and to US 2005/261271, EP 1586571 and WO 2005/095381.

The term "carmegliptin" as employed herein refers to carmegliptin and pharmaceutically acceptable salts thereof, including hydrates and solvates thereof, and crystalline forms thereof A process for preparing this compound (specifically its dihydrochloride salt) is also disclosed in WO 2008/031749, WO 2008/031750 and WO 2008/055814. This compound can be formulated in a pharmaceutical composition as described in WO 2007/017423. For details, e.g. on a process to manufacture, to formulate or to use this compound or a salt thereof, reference is thus made to these documents and to WO 2005/000848.

The term "melogliptin" as employed herein refers to melogliptin and pharmaceutically acceptable salts thereof, including hydrates and solvates thereof, and crystalline forms thereof Methods for its preparation are inter alia disclosed in WO 2006/040625 and WO 2008/001195. Specifically claimed salts include the methanesulfonate and p-toluenesulfonate. For details, e.g. on a process to manufacture, to formulate or to use this compound or a salt thereof, reference is thus made to these documents.

The term "dutogliptin" as employed herein refers to dutogliptin (or PHX-1149, PHX-1149T) and pharmaceutically acceptable salts thereof, including hydrates and solvates thereof, and crystalline forms thereof. Methods for its preparation are inter alia disclosed in WO 2005/047297. Pharmaceutically acceptable salts include the tartrate. For details, e.g. on a process to manufacture, to formulate or to use this compound or a salt thereof, reference is thus made to these documents.

The disclosure of each of the foregoing documents cited above in connection with the specified DPP IV inhibitors is specifically incorporated herein by reference in its entirety.

SGLT-2 inhibitors that may be used in accordance with the invention include, but are not limited to dapagliflozin, canagliflozin, atigliflozin, remogliflozin and sergliflozin.

The term "dapagliflozin" as employed herein refers to dapagliflozin, including hydrates and solvates thereof, and crystalline forms thereof. The compound and methods of its synthesis are described in WO 03/099836 for example. Preferred hydrates, solvates and crystalline forms are described in the patent applications WO 2008/116179 and WO 2008/002824 for example.

The term "canagliflozin" as employed herein refers to canagliflozin, including hydrates and solvates thereof, and crystalline forms thereof and has the following structure: The compound and methods of its synthesis are described in WO 2005/012326 and WO 2009/035969 for example. Preferred hydrates, solvates and crystalline forms are described in the patent applications WO 2008/069327 for example.

The term "atigliflozin" as employed herein refers to atigliflozin, including hydrates and solvates thereof, and crystalline forms thereof. The compound and methods of its synthesis are described in WO 2004/007517, for example.

The term "remogliflozin" as employed herein refers to remogliflozin and prodrugs of remogliflozin, in particular remogliflozin etabonate, including hydrates and solvates thereof, and crystalline forms thereof. Methods of its synthesis are described in the patent applications EP 1213296 and EP 1354888 for example.

The term "sergliflozin" as employed herein refers to sergliflozin and prodrugs of sergliflozin, in particular sergliflozin etabonate, including hydrates and solvates thereof, and crystalline forms thereof. Methods for its manufacture are described in the patent applications EP 1344780 and EP 1489089 for example.

Accordingly, in one embodiment, provided herein are combination therapies comprising, at least, the following combination of agents:

1) a compound of Formula I and miglitol; a compound of Formula I and glipizide; a compound of Formula I and glyburide; a compound of Formula I and saxagliptin; a compound of Formula I and sitagliptin; a compound of Formula I and vildagliptin; a compound of Formula I and linagliptin; a compound of Formula I and dutogliptin; a compound of Formula I and metformin; a compound of Formula I, metformin, and sitagliptin;

2) a compound of Formula II and miglitol; a compound of Formula II and glipizide; a compound of Formula II and glyburide; a compound of Formula II and saxagliptin; a compound of Formula II and sitagliptin; a compound of Formula II and vildagliptin; a compound of Formula II and linagliptin; a compound of Formula II and dutogliptin; a compound of Formula II and metformin; and a compound of Formula II, metformin, and sitagliptin.

In an additional embodiment, the combination therapies of paragraphs 1 and 2, above, can be further combined with compounds of Formula I and/or II.

Pharmaceutical Compositions

The tri-salts of the present invention are suitable as active agents in pharmaceutical compositions that are efficacious particularly for treating diabetes, obesity, and related conditions. The pharmaceutical composition in various embodiments has a pharmaceutically effective amount of the present active agent along with other pharmaceutically acceptable excipients, carriers, fillers, diluents and the like. Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Methods of preparing various pharmaceutical compositions with a specific amount of active compound are known, or will be apparent, to those skilled in this art. For examples, see 'Remington's Pharmaceutical Sciences', Mack Publishing Company, Easter, Pa., 15th Edition (1975).

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Dosage

For administration to human patients, the total daily dose of the compounds of the invention is typically in the range of 0.25 g-6 g, 0.25 g-4 g, 0.25 g-2 g, or 0.25 g-1 g, depending, of course, on the mode of administration. In one embodiment the total daily dose is in the range 1 g to 10 g and in another embodiment the total daily dose is in the range 1 g to 6 g. The total daily dose may be administered in single or divided doses.

These dosages are based on an average human subject having a weight of about 65 kg to 70 kg. The physician will readily be able to determine doses for subjects whose weight falls outside this range, such as infants and the elderly.

Methods of preparing various pharmaceutical compositions with a specific amount of active compound are known, or will be apparent, to those skilled in this art. For examples, see Remington's Pharmaceutical Sciences, Mack Publishing Company, Easter, Pa., 15th Edition (1975).

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Kits

Advantageously, the present invention also provides kits for use by a consumer for treating disease. The kits comprise a) a pharmaceutical composition comprising a tri-salt of the invention and a pharmaceutically acceptable carrier, vehicle or diluent; and, optionally, b) instructions describing a method of using the pharmaceutical composition for treating the specific disease.

A "kit" as used in the instant application includes a container for containing the separate unit dosage forms such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc. . . . "Second Week, Monday, Tuesday, . . . " etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter, which indicates the number of daily doses that, has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

One embodiment of the present invention relates to a kit comprising a unit dosage comprising a compound of the invention with instructions on how to use the kit and with provision for at least one container for holding the unit dosage form.

Methods of Making

The tri-salts of the invention can be prepared using any number of synthesis techniques known to the skilled artisan.

The compound of Formula II, wherein $R^-$ is eicosapentaenoate and n is 1, can be prepared by reacting one equivalent of aspartic acid with two equivalents of metformin free base followed by one equivalent of EPA. The solvents for conducting the reaction can be alcoholic solvents, such as ethanol, methanol, propanol, and isopropanol, ketonic solvents, such as acetone, ethyl methyl ketone, and methyl isopropyl ketone, acetonitrile. The reaction can be conducted at a temperature from between 0° C. to reflux temperature of the solvent used. The reaction time is determined by completion of reaction as monitored by analytical techniques, such as high pressure liquid chromatography.

The compound of Formula II, wherein $R^-$ is eicosapentaenoate and n is 2, can be prepared according to the procedure described above, except that aspartic acid is replaced by glutamic acid.

The compound of Formula II, wherein $R^-$ is docosahexaenoate and n is 1, can be prepared by reacting one equivalent of aspartic acid with two equivalents of metformin free base followed by one equivalent of DHA. The solvents for conducting the reaction can be alcoholic solvents, such as ethanol, methanol, propanol, and isopropanol, ketonic solvents, such as acetone, ethyl methyl ketone, and methyl isopropyl ketone, acetonitrile. The reaction can be conducted at a temperature from between 0° C. to reflux temperature of the solvent used. The reaction time is determined by completion of reaction as monitored by analytical techniques, such as high pressure liquid chromatography.

The compound of Formula II, wherein $R^-$ is docosahexaenoate and n is 2, can be prepared according to the procedure described above, except that aspartic acid is replaced by glutamic acid.

EXEMPLIFICATION

Animal Models

The following example describes a diabetic rat model that may be used for determination of conditions leading to a method for treatment and prevention of post-ischemic damage of the heart and heart tissue.

Spontaneously diabetic Bio-Bred (BB/W) rats are considered a useful model of autoimmune human insulin-dependent diabetes DM). vLike human IDDM, spontaneous diabetes appears during adolescence, with an abrupt clinical onset characterized by weight loss, hyperglycemia, hypoinsulinemia, and ketonuria. As in the case of human diabetics, pathological changes in retina, myocardium, liver, kidney, bone metabolism and peripheral nerves have all been well documented in BB rats, as described in *Diab. Metab. Rev.*, 8:9 (1992).

Isolated Perfused Heart Model

This example describes an isolated perfused rat heart model used in development of the invention. Studies are performed using an isovolumic isolated rat heart preparation. Acutely diabetic male BB/W rats and non-diabetic age-matched (3 to 4 months old) control are pretreated with heparin (1000 u; IP), followed by sodium pentobarbital (65 mg/kg; IP). After deep anaesthesia is achieved as determined by the absence of a foot reflex, the hearts are rapidly excised and placed into iced saline. The arrested hearts are retrograde perfused in a non-recirculating model through the aorta within 2 minutes following their excision. Left ventricular developed pressure (LVDP) is determined using a latex balloon in the left ventricle with high pressure tubing connected to a pressure transducer. Perfusion pressure is monitored using high pressure tubing off the perfusion line. Hemodynamic measurements are recorded on a 4-channel Gould recorder. The system has two parallel perfusion lines with separate oxygenators, pumps and bubble traps, but common temperature control allows rapid change perfusion media. The hearts are perfused using an accurate roller pump. The perfusate consists of 118 mM NaCl, 0.47 mM KCl, 12 mM $CaCl_2$, 12 mM MgCl2, 25 mM $NaHCO_3$, and the substrate 11 mM glucose. The perfusion apparatus is tightly temperature-controlled, with heated baths being used for the perfusate and for the water jacketing around the perfusion tubing to maintain heart temperature at 37±0.5° C. under all conditions. The oxygenated perfusate in the room temperature reservoir is passed through 25 ft. of thin-walled silicone tubing surrounded by distilled water at 37° C. saturated with 95% oxygen.

The perfusate then enters the water-jacketed (37° C.) tubing leading to the heart through a water jacketed bubble trap. This preparation provides excellent oxygenation that routinely has been stable for 3 to 4 hours.

Model for Zero-/Low Ischemia

This example describes a procedure used for study of zero-flow ischemia in diabetic control, diabetic treated, non-diabetic treated and control isolated hearts. Diabetic control (DC) diabetic treated (DZ) normal (C) control and normal treated (CZ) hearts are subjected to 20 minutes of normoxic perfusion followed by 20 minutes of zero-flow ischemia where the perfusate flow is completely shut off, followed by 60 minutes of reperfusion. Hearts are treated with 10 µM metformin eicosapentaenoate. In the metformin eicosapentaenoate treated diabetic group (DZ), hearts are subjected to 10 minutes of normoxic perfusion with normal Krebs-Henseleit buffer and 10 minutes of normoxic perfusion with Krebs-Henseleit buffer containing 10 µM metformin eicosapentaenoate. The hearts are then subjected to 20 minutes of zero-flow ischemia followed by 60 minutes of reperfusion. In order to avoid any variability in reperfusion conditions, both DC and DZ hearts are reperfused with normal Krebs-Henseleit buffer.

Model for Low Flow Ischemia

This example describes a procedure used for study of low-flow ischemia in diabetic controls, diabetic treated, non-diabetic treated and non-diabetic control isolated hearts. Diabetic control hearts (DC) are subjected to 20 minutes of normoxic perfusion at a flow rate of 12.5 mL/minute followed by 30 minutes of low-flow ischemia where the perfusate flow is slowed down to 1.25 mL/min, that is about 10% of normal perfusion, followed by 30 minutes of reperfusion at a normal flow rate (12.5 mL/min) In the metformin eicosapentaenoate treated diabetic or non-diabetic groups (DZ or CZ), hearts are subjected to 10 minutes of normoxic perfusion (flow rate 12.5 mL/min) with normal Krebs-Henseleit buffer and 10 minutes of normoxic perfusion with Krebs-Henseleit buffer containing 10 µM metformin eicosapentaenoate. The hearts are subjected to 30 minutes of low-flow ischemia (flow rate 1.25 mL/min) and 30 minutes of reperfusion at normal flow rate (12.5 mL/min).

Animal models to determine the effects of compounds of the invention on diabetes and complications of diabetes have been reviewed by Tirabassi et al., *ILAR Journal*, 2004, 45, 292-302. Antidiabetic activity may also be tested according to protocols described in the following patents: U.S. Pat. Nos. 4,340,605; 4,342,771; 4,367,234; 4,617,312; 4,687,777 and 4,703,052. Additional references relevant to this application include the following: French Patent 2796551 and U.S. Published Patent Application No. 20030220301.

Example 1

Preparation of Bis[{[dimethylamino)(imino)methyl]amino}(imino)methanaminium](2S)-2-amininium (5Z,8Z,11Z,14Z,17Z)-icosa-5,8,11,14,17-pentaenoate-pentanedioate (Met2-Glu-EPA)

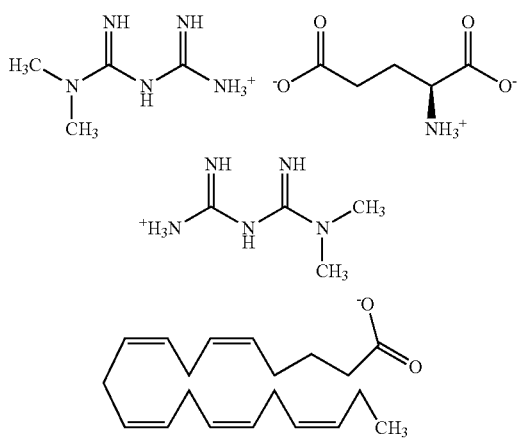

Step 1—Preparation of Bis[{[dimethylamino)(imino)methyl]amino}(imino)methanaminium](2S)-2-aminopentanedioate

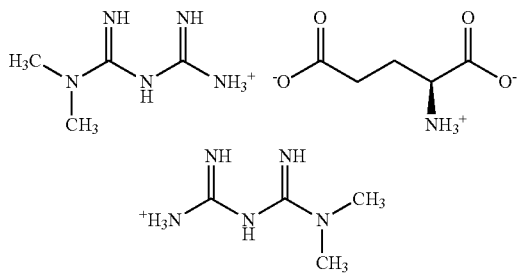

A solution of N,N-dimethylimidodicarbonimidic diamide (1.00 g, 7.74 mmol) in methanol (40 mL) is treated with a solution of L-glutamic acid (0.570 g, 3.87 mmol) in methanol (40 mL) at room temperature (RT) under $N_2$. The mixture is stirred at RT for ½ hr. The methanol is evaporated and the remaining oil is triturated with $CH_3CN$ to give a white solid. The solid is dried at RT under hi-vac for 3 hrs, then stirred in $CH_3CN$ (50 ml) at RT for 2 hrs. The solid is collected by filtration and dried under hi-vac at RT for 1 hr to give 1.3 g (90% yield) of bis[ {[(dimethylamino)(imino)methyl]amino}-(imino)methanaminium](2S)-2-aminopentanedioate as a white solid. $^1$H NMR (300 MHz, MeOD) δ 1.88 (m, 1H) 2.06 (m, 2H) 2.30 (m, 2H) 3.05 (s, 12H) 4.91 (s, 14H); MS (ESI-) for $C_5H_9NO_4$ m/z 146 (M-H)$^-$. MS (ESI+) for $C_4H_{11}N_5$ m/z 130 (M+H)+. Anal Calcd for $C_{13}H_{31}N_{11}O_4$ plus 0.75% $H_2O$: C, 38.22; H, 7.73; N, 37.71. Found: C, 38.57; H, 7.65; N, 36.73.

Step 2—Preparation of Bis[{[(dimethylamino)(imino) methyl]amino}(imino)methanaminium](2S)-2-amininium (5Z,8Z,11Z,14Z,17Z)-icosa-5,8,11,14,17-pentaenoate-pentanedioate (Met2-Glu-EPA)

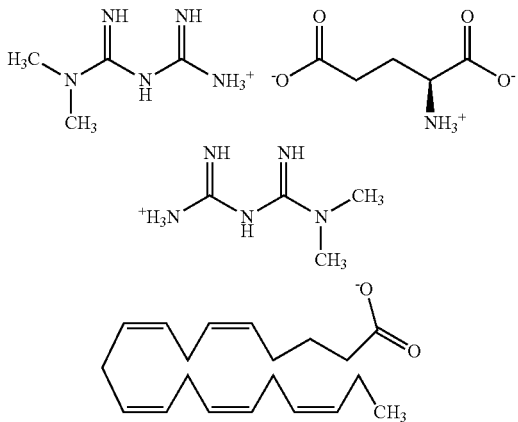

A solution of bis[{[(dimethylamino)(imino)methyl] amino}(imino)methanaminium](2S)-2-aminopentanedioate (4.28 g, 15.5 mmol) in methanol (180 mL) is stirred with (5Z,8Z,11Z,14Z,17Z)-eicosa-5,8,11,14,17-pentaenoic acid (5.15 g, 17.0 mmol) at RT in an amber flask under $N_2$ for 1 hour. The methanol is evaporated and the remaining oil is triturated with ice cold $CH_3CN$ (50 ml) to form a solid. This solid is collected by filtration in the dark and dried at RT in the dark under hi-vac. Yield=10 g (91% yield) of bis[{[dimethylamino)(imino)methyl]amino}(imino)methanaminium] (2S)-2-amininium (5Z,8Z,11Z,14Z,17Z)-eicosa-5,8,11,14,17-pentaenoate-pentanedioate as a light tan solid. $^1$H NMR (300 MHz, MeOD) δ 0.92 (t, 3H) 1.67 (m, 2H) 2.10 (m, 8H) 2.47 (m, 2H) 2.86 (m, 8H) 3.05 (s, 12H) 3.57 (m, 1H) 4.88 (m, 15H) 5.37 (m, 10H); MS (ESI−) for $C_{20}H_{30}O_2$ m/z 301 (M−); Anal Calcd for $C_{33}H_{61}N_{11}O_6$ plus 1.26% $H_2O$: C, 55.28; H, 8.72; N, 21.49. Found: C, 55.24; H, 8.71; N, 20.81. MP=127-130° C. (Softens @ 100° C.).

Example 2

Bis[{[dimethylamino)(imino)methyl]amino}(imino) methanaminium](2S)-2-amininium (5Z,8Z,11Z,14Z,17Z)-eicosa-5,8,11,14,17-pentaenoate-pentanedioate (Met2-Glu-EPA)-Stoichiometric Combination Method

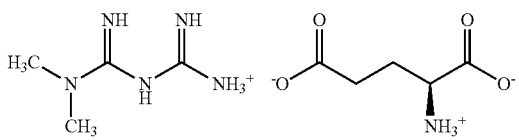

-continued

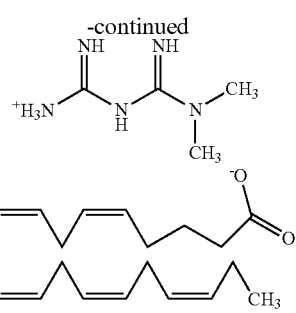

(5Z,8Z,11Z,14Z,17Z)-eicosa-5,8,11,14,17-pentaenoic acid (6.79 g, 22.4 mmol) is added to a mixture of L-glutamic acid (3.30 g, 22.4 mmol) and N,N-dimethylimidodicarbonimidic diamide (5.80 g, 44.9 mmol) (recrystallized from EtOAc) in 400 ml of methanol under $N_2$. The mixture is stirred at RT for ½ hour and a small amount of a precipitate forms. The methanol is evaporated and the resulting homogeneous oil is taken up in $CH_3CN$ (300 ml). A solid forms and the $CH_3CN$ is evaporated. The solid is dried under hi-vac over $P_2O_5$ at 40° C. overnight to give 13.52 g (85% yield) of bis[{[(dimethylamino)(imino)methyl]amino}(imino)methanaminium](2S)-2-amininium (5Z,8Z,11Z,14Z,17Z)-eicosa-5,8,11,14,17-pentaenoate-pentanedioate as a tan solid. $^1$H NMR (300 MHz, MeOD) δ 0.92 (t, 3H) 1.67 (m, 2H) 2.10 (m, 8H) 2.47 (m, 2H) 2.86 (m, 8H) 3.05 (s, 12H) 3.57 (m, 1H) 4.88 (m, 15H) 5.37 (m, 10H); MS (ESI−) for $C_{20}H_{30}O_2$ m/z 301 (M) Anal Calcd for $C_{13}H_{31}N_{11}O_4$ plus 0.87% $H_2O$: C, 55.40; H, 8.69; N, 21.79. Found: C, 55.30; H, 8.50; N, 21.65.

Example 3

Bis[{[dimethylamino)(imino)methyl]amino}(imino) methanaminium]-(5Z,8Z,11Z,14Z,17Z)-eicosa-5,8, 11,14,17-pentaenoate-(3S)-3-ammonio-3-carboxypropanoate (Met2-Asp-EPA)

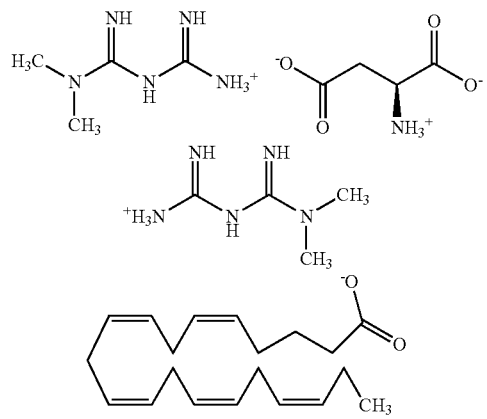

A mixture of L-aspartic acid (2.90 g, 21.8 mmol), (5Z,8Z, 11Z,14Z,17Z)-eicosa-5,8,11,14,17-pentaenoic acid (6.60 g, 21.8 mmol) and N,N-dimethylimidodicarbonimidic diamide (5.64 g, 43.7 mmol) in methanol (300 mL) was warmed in a 60° C. oil bath for 30 minutes. Solids all dissolved. After stirring for another hour at 60° C., the mixture was allowed to cool to RT, evaporated in vacuo and left to dry on high vac overnight to yield a tan solid, 14.93 g (99%). $^1$H NMR (300 MHz, MeOD) δ ppm 0.97 (t, J=7.54 Hz, 3H) 1.53-1.78 (m, 2H) 1.96-2.28 (m, 6H) 2.57 (dd, J=17.23, 10.15 Hz, 1H) 2.73-2.92 (m, 9H) 3.04 (s, 12H) 3.73 (dd, J=10.15, 3.54 Hz, 1H) 4.89 (br. s., 15H) 5.18-5.51 (m, 10H). MS (ESI−) for $C_4H_7NO_4$ m/z 132 (M−H)−. MS (ESI−) for $C_{20}H_{30}O_2$ m/z 301 (M−H)−. MS (ESI+) for $C_4H_{11}N_5$ m/z 130 (M+H)+. Anal Calcd for $C_{32}H_{59}N_{11}O_6$: C, 55.39; H, 8.57; N, 22.20. Found: C, 55.03; H, 8.81; N, 21.76.

Example 4

Rat Pharmacokinetics of Di-Metformin Glutamate Eicosapentaenoate

Single dose oral pharmacokinetic parameters for di-metformin glutamate eicosapentaenoate, prepared by the procedure described in Example 1, were determined in Sprague-Dawley rats. Di-metformin glutamate eicosapentaenoate was administered by oral gavage as an aqueous solution in 0.5% carboxymethyl cellulose to 6 rats, 3 males and 3 females. Rats were dosed at 52 mg/kg. Blood samples were obtained from each rat by jugular vein catheter. Samples were collected at 0.25, 0.5, 1, 2, 4, 8, 12, and 24 hours post dose. Blood samples were centrifuged to separate red blood cells and the resulting plasma samples were analyzed for eicosapentaenoic acid. Calculated pharmacokinetic parameters shown below in Table 1 are mean values from 6 rats.

TABLE 1

Rat Oral Pharmacokinetic Parameters for Di-metformin glutamate Eicosapentaenoate

| Analyte | EPA | Metformin |
| --- | --- | --- |
| $C_{max}$ (μg/mL) | 14.97 | 2.07 |
| $T_{max}$ (h) | 0.5 | 1.0 |
| AUC (0-24) (μg*h/mL) | 228.67 | 8.49 |

Combination Therapy: Pharmacological Examples
Treatment of Type 2 Diabetes

Treating patients with type 2 diabetes with the pharmaceutical composition according to the invention, in addition to producing an acute improvement in the glucose metabolic situation, prevents a deterioration in the metabolic situation in the long term. This can be observed when patients are treated for a longer period, e.g. 3 months to 1 year or even 1 to 6 years, with the pharmaceutical composition according to the invention and are compared with patients who have been treated with other antidiabetic medicaments. There is evidence of therapeutic success compared with patients treated with other antidiabetic medicaments if no or only a slight increase in the fasting glucose and/or HbA1c value is observed. Further evidence of therapeutic success is obtained if a significantly smaller percentage of the patients treated with a pharmaceutical composition according to the invention, compared with patients who have been treated with other medicaments, undergo a deterioration in the glucose metabolic position (e.g. an increase in the HbA1c value to >6.5% or >7%) to the point where treatment with an additional oral antidiabetic medicament or with insulin or with an insulin analogue is indicated.

Treatment of Insulin Resistance

In clinical studies running for different lengths of time (e.g. 2 weeks to 12 months) the success of the treatment is checked using a hyperinsulinaemic euglycaemic glucose clamp study. A significant rise in the glucose infusion rate at the end of the study, compared with the initial value or compared with a placebo group, or a group given a different therapy, proves the efficacy of a pharmaceutical composition according to the invention in the treatment of insulin resistance.

Treatment of Hyperglycaemia

In clinical studies running for different lengths of time (e.g. 1 day to 24 months) the success of the treatment in patients with hyperglycaemia is checked by determining the fasting glucose or non-fasting glucose (e.g. after a meal or a loading test with oGTT or a defined meal). A significant fall in these glucose values during or at the end of the study, compared with the initial value or compared with a placebo group, or a group given a different therapy, proves the efficacy of a pharmaceutical composition according to the invention in the treatment of hyperglycaemia.

Treatment of Metabolic Syndrome

The efficacy of a pharmaceutical composition according to the invention can be tested in clinical studies with varying run times (e.g. 12 weeks to 6 years) by determining the fasting glucose or non-fasting glucose (e.g. after a meal or a loading test with oGTT or a defined meal) or the HbA1c value. A significant fall in these glucose values or HbA1c values during or at the end of the study, compared with the initial value or compared with a placebo group, or a group given a different therapy, proves the efficacy of an active ingredient or combination of active ingredients in the treatment of Metabolic Syndrome. Examples of this are a reduction in systolic and/or diastolic blood pressure, a lowering of the plasma triglycerides, a reduction in total or LDL cholesterol, an increase in HDL cholesterol or a reduction in weight, either compared with the starting value at the beginning of the study or in comparison with a group of patients treated with placebo or a different therapy.

Prevention of Micro- or Macrovascular Complications

The treatment of type 2 diabetes or pre-diabetes patients with a pharmaceutical composition according to the invention prevents or reduces or reduces the risk of developing microvascular complications (e.g. diabetic neuropathy, diabetic retinopathy, diabetic nephropathy, diabetic foot, diabetic ulcer) or macrovascular complications (e.g. myocardial infarct, acute coronary syndrome, unstable angina pectoris, stable angina pectoris, stroke, peripheral arterial occlusive disease, cardiomyopathy, heart failure, heart rhythm disorders, vascular restenosis). Type 2 diabetes or patients with pre-diabetes are treated long-term, e.g. for 1-6 years, with a pharmaceutical composition according to the invention or a combination of active ingredients according to the invention and compared with patients who have been treated with other antidiabetic medicaments or with placebo. Evidence of therapeutic success compared with patients who have been treated with other antidiabetic medicaments or with placebo can be found in the smaller number of single or multiple complications. In the case of macrovascular events, diabetic foot and/or diabetic ulcer, the numbers are counted by anamnesis and various test methods. In the case of diabetic retinopathy the success of the treatment is determined by computer-controlled illumination and evaluation of the background to the eye or other ophthalmic methods. In the case of diabetic neuropathy, in addition to anamnesis and clinical examination, the nerve conduction rate can be measured using a calibrated tuning fork, for example. With regard to diabetic nephropathy the following parameters may be investigated before the start, during and at the end of the study: secretion of albumin, creatinine clearance, serum creatinine values, time taken for the serum creatinine values to double, time taken until dialysis becomes necessary.

Formulation Examples

Combination Therapy

The following examples of formulations, which may be obtained analogously to methods known in the art, serve to illustrate the present invention more fully without restricting it to the contents of these examples. The term "active ingredient" denotes two compounds according to the invention, i.e., denotes The term "active ingredient" denotes two compounds according to the invention, i.e., denotes a compound of Formula I or II, or a mixture thereof (first component of the active ingredient) and other antidiabetic agents such as statins, cholesterol absorption inhibitors, and CETP inhibitors or a pharmaceutically-acceptable salt or prodrug thereof, or a pharmaceutically-acceptable salt of said prodrug (second component of the active ingredient). Additional suitable formulations may be prepared according to the procedures described in, for example in the application WO 2007/128724, and in the U.S. Patent Application, 2010/032011 the disclosure of which are incorporated herein in its entirety. Additional suitable formulations for the sulfonylureas, DPP IV inhibitors may be those formulations which are available on the market, or formulations described in the patent applications cited above in paragraph "background of the invention", or those described in the literature, for example as disclosed in current issues of "Rote Liste S" (Germany) or of "Physicians Desk Reference"

Example 1

| Tablet Containing 1000 mg of Active Ingredient | |
|---|---|
| Composition | |
| (1) Active ingredient | 1000 mg |
| (2) Mannitol | 100 mg |
| (3) Maize starch | 50 mg |
| (4) Polyvinyl pyrrolidone | 15 mg |
| (5) Magnesium stearate | 2 mg |
| | 1167 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm

Example 2

| Tablet Containing 1050 mg of Active Ingredient | |
|---|---|
| Composition | |
| (1) Active ingredient | 1050 mg |
| (2) Mannitol | 100 mg |
| (3) Maize starch | 50 mg |
| (4) Polyvinyl pyrrolidone | 15 mg |
| (5) Magnesium stearate | 2 mg |
| | 1217 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm

Example 3

| Tablet Containing 1100 mg of Active Ingredient | |
|---|---|
| Composition | |
| (1) Active ingredient | 1100 mg |
| (2) Mannitol | 100 mg |
| (3) Maize starch | 50 mg |
| (4) Polyvinyl pyrrolidone | 15 mg |
| (5) Magnesium stearate | 2 mg |
| | 1267 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm

Example 4

| Capsules Containing 1050 mg of Active Ingredient | |
|---|---|
| Composition | |
| (1) Active ingredient | 1050 mg |
| (2) Mannitol | 100 mg |
| (3) Maize starch | 50 mg |
| (4) Polyvinyl pyrrolidone | 15 mg |
| (5) Magnesium stearate | 2 mg |
| | 1217 mg |

Preparation:

(1) is triturated with (3). This trituration is added to the mixture of (2) and (4) with vigorous mixing. This powder mixture is packed into size 3 hard gelatin capsules in a capsule filling machine.

Example 5

| Capsules Containing 1100 mg of Active Ingredient | |
|---|---|
| Composition | |
| (1) Active ingredient | 1100 mg |
| (2) Mannitol | 100 mg |
| (3) Maize starch | 50 mg |
| (4) Polyvinyl pyrrolidone | 15 mg |
| (5) Magnesium stearate | 2 mg |
| | 1267 mg |

Preparation:

(1) is triturated with (3). This trituration is added to the mixture of (2) and (4) with vigorous mixing. This powder mixture is packed into size 3 hard gelatin capsules in a capsule filling machine.

The invention claimed is:

1. A composition comprising a salt of metformin, an amino acid, and a polyunsaturated fatty acid, the salt having the structure of Formula II $$\text{(II)}$$

wherein R⁻ is a polyunsaturated fatty acid, and n is 1 or 2, and an anti-hyperlipidemic agent, an anti-hyperglycemic agent, or both.

2. The composition of claim 1, wherein R⁻ is eicosapentaenoate or docosahexaenoate.

3. The composition of claim 1, wherein R⁻ is eicosapentaenoate or docosahexaenoate, and n is 1.

4. The composition of claim 1, wherein R⁻ is eicosapentaenoate or docosahexaenoate, and n is 2.

5. The composition of claim 1 further comprising a pharmaceutically acceptable carrier, vehicle or diluent.

6. The composition of claim 1, wherein the anti-hyperlipidemic agent is selected from a statin, an HMG CoA enzyme inhibitor, a cholesterol absorption inhibitor, or a cholesterol esterase transfer protein (CETP) inhibitor.

7. The composition of claim 6, wherein the anti-hyperlipidemic agent is a statin.

8. The composition of claim 7, wherein the statin is selected from the group consisting of atorvastatin, simvastatin, pravastatin, lovastatin, fluvastatin, rosuvastatin, cerivastatin, mevastatin, rivastatin, pitavastatin, nisvastatin, itavastatin, velostatin and fluindostatin, pharmaceutically-acceptable salts or prodrugs thereof, and pharmaceutically-acceptable salts of said prodrugs.

9. The composition of claim 8, wherein the statin is selected from atorvastatin, rosuvostatin, simvastatin, or pravastatin.

10. The composition of claim 1, wherein the anti-hyperglycemic agent is selected from the group consisting of sulfonylureas, meglitinides, thiazolidinediones, alpha-glucosidase inhibitors, DPP IV inhibitors, SGLT-2 inhibitors and pharmaceutically-acceptable salts and prodrug thereof, and pharmaceutically-acceptable salts of said prodrug.

11. The composition of claim 10, wherein the anti-hyperglycemic agent is a DPP IV inhibitor or an SGLT-2 inhibitor.

12. The composition of claim 11, wherein the DPP IV inhibitor is selected from the group consisting of sitagliptin, linagliptin, vildagliptin, saxagliptin, alogliptin, denagliptin, carmegliptin, melogliptin, dutogliptin and pharmaceutically-acceptable salts and prodrugs thereof, and pharmaceutically-acceptable salts of said prodrugs.

13. The composition of claim 11, wherein the SGLT-2 inhibitor is selected from the group consisting of dapagliflozin canagliflozin, atigliflozin, remogliflozin, sergliflozin, and pharmaceutically-acceptable salts and prodrugs thereof, and pharmaceutically-acceptable salts of said prodrugs.

14. The composition of claim 1, wherein the composition comprises an anti-hyperlipidemic agent.

15. The composition of claim 14, wherein R⁻ is eicosapentaenoate or docosahexaenoate.

16. The composition of claim 14, wherein R⁻ is eicosapentaenoate or docosahexaenoate, and n is 1.

17. The composition of claim 14, wherein R⁻ is eicosapentaenoate or docosahexaenoate, and n is 2.

18. The composition of claim 1, wherein the composition comprises an anti-hyperglycemic agent.

19. The composition of claim 18, wherein R⁻ is eicosapentaenoate or docosahexaenoate.

20. The composition of claim 18, wherein R⁻ is eicosapentaenoate or docosahexaenoate, and n is 1.

21. The composition of claim 18, wherein R⁻ is eicosapentaenoate or docosahexaenoate, and n is 2.

22. A kit comprising a) a unit dosage form comprising the composition of claim 1, b) instructions on how to use the kit; and c) at least one container for holding the unit dosage form.

23. A method for treating diabetes or lowering triglycerides in a subject in need thereof, the method comprising administering to the subject a therapeutically effective amount of the composition of claim 1.

24. The method of claim 23, further comprising administering metformin (free base), or a salt form of metformin.

25. The method of claim 24, wherein the salt form of metformin is metformin docosahexaenoate, metformin eicosapentaenoate, metformin hydrochloride, metformin succinate, or metformin fumarate.

26. The method of claim 23, wherein the subject is a mammal.

27. The method of claim 23, wherein the subject is a human.

28. The method of claim 23, wherein the composition comprises an anti-hyperglycemic agent selected from the group consisting of sulfonylureas, meglitinides, thiazolidinediones, alpha-glucosidase inhibitors, DPP IV inhibitors, SGLT-2 inhibitors and pharmaceutically-acceptable salts and prodrug thereof, and pharmaceutically-acceptable salts of said prodrug.

29. The method of claim 28, wherein the anti-hyperglycemic agent is a DPP IV inhibitor or an SGLT-2 inhibitor.

30. The method of claim 29, wherein the DPP IV inhibitor is selected from the group consisting of sitagliptin, linagliptin, vildagliptin, saxagliptin, alogliptin, denagliptin, carmegliptin, melogliptin, dutogliptin and pharmaceutically-acceptable salts and prodrugs thereof, and pharmaceutically-acceptable salts of said prodrugs.

31. The method of claim 30, wherein the SGLT-2 inhibitor is selected from the group consisting of dapagliflozin canagliflozin, atigliflozin, remogliflozin, sergliflozin, and pharmaceutically-acceptable salts and prodrugs thereof, and pharmaceutically-acceptable salts of said prodrugs.

32. A method for treating cardiovascular disease in a subject in need thereof, the method comprising administering to the subject a therapeutically effective amount of the composition of claim 14.

33. The method of claim 32, wherein the cardiovascular disease is selected from the group consisting of cardiac arrhythmia, cardiac ischemia, myocardial infarction, cardiomyopathy, and stroke.

34. The method of claim 33, wherein the cardiovascular disease is myocardial infarction or stroke.

35. The method of claim 32, wherein the subject is mammal.

36. The method of claim 34, wherein subject is human.

37. The method of claim 32, wherein the anti-hyperlipidemic agent is selected from a statin, an HMG CoA enzyme inhibitor, a cholesterol absorption inhibitor, or a cholesterol esterase transfer protein (CETP) inhibitor.

38. The method of claim 37, wherein the anti-hyperlipidemic agent is a statin.

39. The method of claim 38, wherein the statin is selected from the group consisting of atorvastatin, simvastatin, pravastatin, lovastatin, fluvastatin, rosuvastatin, cerivastatin, mevastatin, rivastatin, pitavastatin, nisvastatin, itavastatin, velostatin and fluindostatin, pharmaceutically-acceptable salts or prodrugs thereof, and pharmaceutically-acceptable salts of said prodrugs.

40. The method of claim 39, wherein the statin is selected from atorvastatin, rosuvostatin, simvastatin, or pravastatin.

* * * * *